United States Patent
Koslover et al.

(10) Patent No.: US 11,066,702 B2
(45) Date of Patent: Jul. 20, 2021

(54) OPTICALLY-BASED NANOPORE ANALYSIS WITH REDUCED BACKGROUND

(71) Applicant: Quantapore, Inc., Menlo Park, CA (US)

(72) Inventors: Daniel Koslover, Menlo Park, CA (US); Brett N. Anderson, Menlo Park, CA (US)

(73) Assignee: Quantapore, Inc., South San Francisco, CA (US)

(*) Notice: Subject to any disclaimer, the term of this patent is extended or adjusted under 35 U.S.C. 154(b) by 0 days.

(21) Appl. No.: 16/064,429

(22) PCT Filed: Jan. 11, 2017

(86) PCT No.: PCT/US2017/013036
§ 371 (c)(1),
(2) Date: Jun. 20, 2018

(87) PCT Pub. No.: WO2017/123647
PCT Pub. Date: Jul. 20, 2017

(65) Prior Publication Data
US 2019/0002971 A1    Jan. 3, 2019

Related U.S. Application Data

(60) Provisional application No. 62/279,503, filed on Jan. 15, 2016, provisional application No. 62/308,145, filed on Mar. 14, 2016.

(51) Int. Cl.
*C12Q 1/68* (2018.01)
*C12Q 1/6869* (2018.01)
(Continued)

(52) U.S. Cl.
CPC ....... *C12Q 1/6869* (2013.01); *G01N 21/6408* (2013.01); *G01N 21/6428* (2013.01);
(Continued)

(58) Field of Classification Search
CPC .... C12Q 1/68; C12Q 1/6869; G01N 21/6408; G01N 21/6428; G01N 33/48721
See application file for complete search history.

(56) References Cited

U.S. PATENT DOCUMENTS 5,973,316 A  10/1999  Ebbesen et al.
6,040,936 A   3/2000  Kim et al.
(Continued)

FOREIGN PATENT DOCUMENTS

WO  WO 2009/022152  2/2009
WO  WO 2011/040996  4/2011
(Continued)

OTHER PUBLICATIONS

Auger, T. et al. "Zero-Mode Waveguide Detection of Flow-Driven DNA Translocation through Nanopores," *Physical Review Letters*, 113(2), 5 pages, Jul. 9, 2014.
(Continued)

*Primary Examiner* — Brian J. Sines
(74) *Attorney, Agent, or Firm* — Levine Bagade Han LLP

(57) ABSTRACT

The invention is directed to nanopore arrays comprising opaque layers that reduce background fluorescence in optical signal collected in applications of such arrays for analyzing molecules. In some embodiments, such arrays are used to determine characteristics of polymers, such as polynucleotides, in methods comprising the steps of translocating polymers through nanopores of such arrays wherein polymers have one or more optical labels, exciting optical labels of the polymers in a signal generation region of each nanopore extending from the opaque layer toward the direction of the excitation beam, detecting optical signals from the signal generation regions of each nanopore to determine characteristics of the polymer translocating therethrough.

8 Claims, 12 Drawing Sheets

(51) Int. Cl.
*G01N 21/64* (2006.01)
*G01N 33/487* (2006.01)
*G01N 33/48* (2006.01)

(52) U.S. Cl.
CPC ....... *G01N 33/48* (2013.01); *G01N 33/48721* (2013.01); *G01N 2021/6432* (2013.01); *G01N 2021/6441* (2013.01)

(56) References Cited

U.S. PATENT DOCUMENTS

| | | | |
|---|---|---|---|
| 6,052,238 | A | 4/2000 | Ebbesen et al. |
| 6,236,033 | B1 | 5/2001 | Ebbesen et al. |
| 6,285,020 | B1 | 9/2001 | Kim et al. |
| 7,056,661 | B2 | 6/2006 | Korlach et al. |
| 7,318,907 | B2 | 1/2008 | Stark et al. |
| 8,168,380 | B2 * | 5/2012 | Chan ................ G01N 33/48721 435/6.1 |
| 8,278,055 | B2 | 10/2012 | Su et al. |
| 8,906,670 | B2 | 12/2014 | Gray et al. |
| 2003/0036204 | A1 | 2/2003 | Stark et al. |
| 2005/0282229 | A1* | 12/2005 | Su ........................ G01N 33/582 435/7.1 |
| 2006/0019247 | A1 | 1/2006 | Su et al. |
| 2008/0099667 | A1 | 5/2008 | Stark et al. |
| 2011/0281740 | A1* | 11/2011 | Beechem ............. C12Q 1/6869 506/7 |
| 2012/0135410 | A1 | 5/2012 | Soni et al. |
| 2014/0335513 | A9 | 11/2014 | Huber et al. |
| 2016/0076091 | A1* | 3/2016 | Huber ................ C12Q 1/6869 435/6.1 |
| 2018/0364169 | A1* | 12/2018 | Anderson ............ C12Q 1/6869 |

FOREIGN PATENT DOCUMENTS

| | | |
|---|---|---|
| WO | WO 2012/121756 | 9/2012 |
| WO | WO 2014/066905 | 5/2014 |
| WO | WO 2014/190322 | 11/2014 |
| WO | WO 2016/057829 | 4/2016 |
| WO | WO 2016/065339 | 4/2016 |
| WO | WO 2016/200737 | 12/2016 |
| WO | WO 2017/100027 | 6/2017 |
| WO | WO 2017/123647 | 7/2017 |
| WO | WO 2018/071273 | 4/2018 |

OTHER PUBLICATIONS

Axelevitch, A. et al. "Investigation of Optical Transmission in Thin Metal Films," *Physics Procedia*, vol. 32, pp. 1-13, 2012.

Foquet, M. et al. "Improved fabrication of zero-mode waveguides for single-molecule detection," *Journal of Applied Physics*, 103(3), 9 pages, Feb. 4, 2008.

Ghaemi, H. F. et al. "Surface plasmons enhance optical transmission through subwavelength holes," *Physical Review B*, 58(11), pp. 6779-6782, Sep. 15, 1998.

Gur, A. et al. "Sub-wavelength and non-periodic hole array based fully lensless imager," *Optics Communications*, 284(14), pp. 3509-3517, Jul. 2011.

Huang, K. et al. "Ultrahigh-capacity non-periodic photon sieves operating in visible light," *Nature Communications*, vol. 6, 7 pages, May 5, 2015.

Korlach, J. et al. "Selective aluminum passivation for targeted immobilization of single DNA polymerase molecules in zero-mode waveguide nanostructures," *Proc Natl Acad Sci*, 105(4), pp. 1176-1181, Jan. 29, 2008.

Larkin, J. et al. "Reversible Positioning of Single Molecules inside Zero-Mode Waveguides," *Nano Letters*, 14(10), pp. 6023-6029, Sep. 11, 2014.

Pacifici, D. et al. "Universal optical transmission features in periodic and quasiperiodic hole arrays," *Optics Express*, 16(12), pp. 9222-9238, Jun. 6, 2008.

PCT International Patent Application No. PCT/US2017/013036 filed Jan. 11, 2017 in the name of Quantapore, Inc., International Preliminary Report on Patentability dated Jul. 26, 2018.

PCT International Patent Application No. PCT/US2017/013036 filed Jan. 11, 2017 in the name of Quantapore, Inc., International Search Report and Written Opinion dated Mar. 31, 2017.

Wei, R. et al. "Fabrication of Metallized Nanopores in Silicon Nitride Membranes for Single-Molecule Sensing," *Small*, 6(13), pp. 1406-1414, Jul. 5, 2010.

\* cited by examiner

OPTICALLY-BASED NANOPORE ANALYSIS WITH REDUCED BACKGROUND This application is a U.S. national application filed under 35 U.S.C. 371 to PCT International Application No. PCT/US2017/013036 filed Jan. 11, 2017, which claims benefit of priority to U.S. Provisional Patent Application Nos. 62/279,503 filed Jan. 15, 2016 and 62/308,145 filed Mar. 14, 2016, each of which are incorporated by reference herein in its entirety.

BACKGROUND

DNA sequencing technologies developed over the last decade have revolutionized the biological sciences, e.g. van Dijk et al, Trends in Genetics, 30(9): 418-426 (2014). However, there remains a host of challenges that must be overcome to achieve the full potential of the technology, including reduction of per-run sequencing cost, simplification of sample preparation, reduction of run times, increasing sequence read lengths, improving data analysis, and the like. Single molecule sequencing techniques, such as nanopore-based sequencing, may address some of these challenges; however, these approaches have their own set of technical difficulties, such as, reliable nanostructure fabrication, control of DNA translocation rates, unambiguous nucleotide discrimination, detection and processing of signals from large arrays of nanoscale sensors, and so on, e.g. Branton et al, Nature Biotechnology, 26(10): 1146-1153 (2008).

Optical detection of nucleotides has been proposed as a potential solution to some of the technical difficulties in the field of nanopore sequencing, for example, the difficulty of collecting independent signals from large arrays of nanopores. However, with fluorescence-based signals, overcoming background noise in the optical detection of single molecules remains a significant challenge. This has led to the frequent use of microscopy systems, such as total internal reflection fluorescence (TIRF) systems, which minimize background excitation, but added complication and expense to the detection systems.

In view of the above, it would be advantageous to nanopore sensor technology in general and its particular applications, such as optically based nanopore sequencing, if methods and devices were available that addressed the background problem of single molecule analysis with the use of simpler and less expensive microscopy systems.

SUMMARY OF THE INVENTION

The present invention is directed to methods and devices for single molecule analysis using optical labels and nanopores. In one aspect, methods and devices of the invention are directed to reducing noise in optical signals generated upon translocation of labeled polymer analytes through nanopores.

In some embodiments, the invention is directed to methods of determining characteristics of polymers, such as polynucleotides, which comprise the following steps: (a) providing a nanopore array comprising a solid phase membrane and an opaque layer co-extensive therewith, the nanopore array comprising a plurality of apertures and separating a first chamber and a second chamber, wherein each aperture provides fluid communication between the first chamber and the second chamber and has a signal generation region and wherein the opaque layer substantially prevents light from passing through the nanopore array; (b) translocating polymers from the first chamber to the second chamber through the apertures, each polymer having one or more optical labels attached thereto capable of generating an optical signal having at least a first wavelength indicative of a characteristic of the polymer; (c) exciting with an excitation beam having a second wavelength the optical labels of the polymers as they translocate through the signal generation regions of the apertures, wherein the optical labels in the detection regions generate optical signals whose first wavelength is different than the second wavelength; and (d) detecting optical signals from the optical labels in the signal generation regions to determine the characteristics of the polymers.

In some embodiments, the invention is directed to methods of determining characteristics of polymers which comprise the following steps: (a) providing a nanopore array comprising a solid phase membrane having a first side, a second side, and a plurality of apertures therethrough, wherein the solid phase membrane separates a first chamber and a second chamber such that each aperture provides fluid communication between the first chamber and the second chamber and wherein the first side of the solid phase membrane has an opaque coating thereon and each aperture has a detection region extending from the opaque coating of the first side toward the second side; (b) translocating polymers from the first chamber to the second chamber through the apertures, each polymer having one or more optical labels attached thereto capable of generating a signal having at least a first wavelength indicative of a characteristic of the polymer; (c) illuminating from the second side of the solid phase membrane the optical labels in the detection regions of the apertures with an excitation beam having a second wavelength so that optical labels in the detection regions generate signals whose first wavelength is different than the second wavelength; (d) detecting signals from the optical labels in the detection regions to determine the characteristics of the polymers.

In other embodiments, the invention is directed to methods of determining characteristics of polymers comprising the steps: (a) providing a nanopore array comprising a solid phase membrane having a first side, a second side, and a plurality of apertures therethrough, wherein the solid phase membrane separates a first chamber and a second chamber such that each aperture provides fluid communication between the first chamber and the second chamber and wherein the second side of the solid phase membrane has an opaque coating thereon and each aperture has a detection region extending from the opaque coating of the second side into the second chamber; (b) translocating polymers from the first chamber to the second chamber through the apertures, each polymer having one or more optical labels attached thereto capable of generating a signal having at least a first wavelength indicative of a characteristic of the polymer; (c) illuminating from the second side of the solid phase membrane the optical labels in the detection regions of the apertures with an excitation beam having a second wavelength so that optical labels in the detection regions generate signals whose first wavelength is different than the second wavelength; and (d) detecting signals from the optical labels in the detection regions to determine the characteristics of the polymers.

In still other embodiments, the invention is directed to methods for determining sequences of polynucleotides comprising the following steps: (a) providing a nanopore array comprising a solid phase membrane and an opaque layer co-extensive therewith, the nanopore array comprising a plurality of apertures and separating a first chamber and a second chamber, wherein each aperture provides fluid communication between the first chamber and the second chamber and has a signal generation region and wherein the opaque layer substantially prevents light from passing through the nanopore array; (b) translocating polynucleotides from the first chamber to the second chamber through the apertures, wherein different kinds of nucleotides of the polynucleotides are labeled with different fluorescent labels that generate distinguishable fluorescent signals and wherein each of said apertures constrains nucleotides of a polynucleotide to move single file through the signal generation region; (c) exciting with an excitation beam the fluorescent labels of the polynucleotides as they translocate through the signal generation regions of the apertures; (d) detecting fluorescent signals from the fluorescent labels in the signal generation regions to determine the characteristics of the polymers; and (e) determining a sequence of nucleotides from the fluorescent signals detected at the signal generation region of each aperture.

The present invention advantageously overcomes the problem of optical noise cause by direct illumination systems in optically-based nanopore analysis. These and other advantages of the present invention are exemplified in a number of implementations and applications, some of which are summarized below and throughout the specification.

DETAILED DESCRIPTION OF THE INVENTION

Figure 1A:
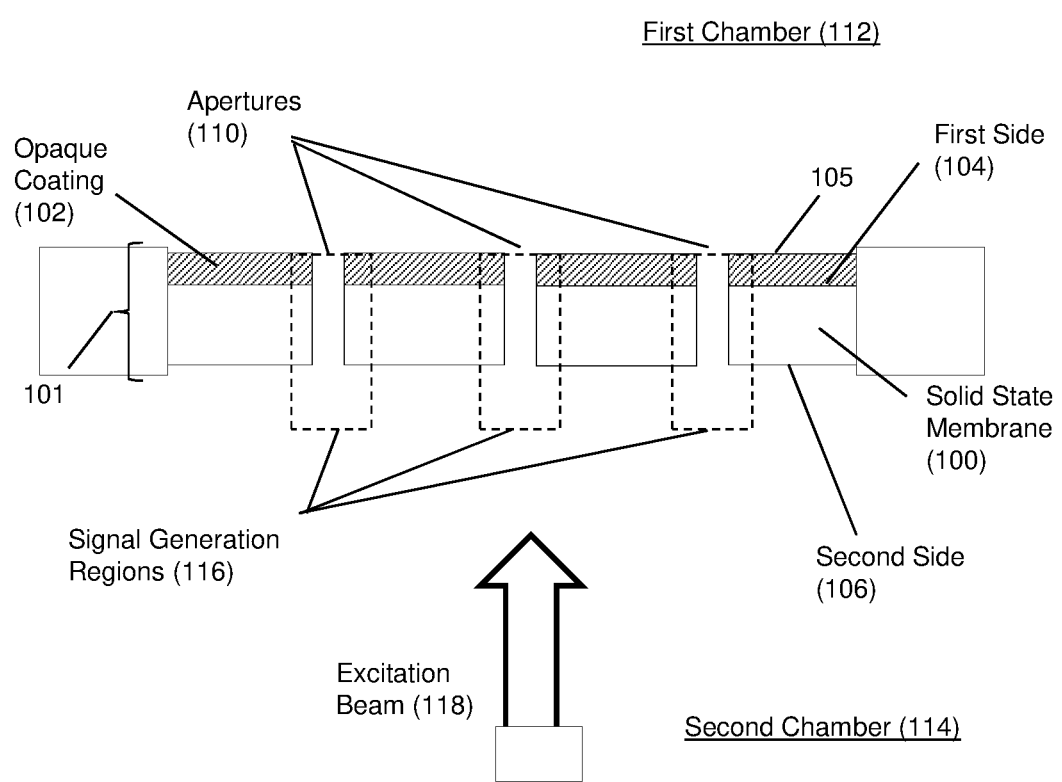
FIGS. 1A-1H illustrates elements of the invention in particular embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, particular nanopore types and numbers, particular labels, FRET pairs, detection schemes, fabrication approaches of the invention are shown for purposes of illustration. It should be appreciated, however, that the disclosure is not intended to be limiting in this respect, as other types of nanopores, arrays of nanopores, and other fabrication technologies may be utilized to implement various aspects of the systems discussed herein. Guidance for aspects of the invention is found in many available references and treatises well known to those with ordinary skill in the art, including, for example, Cao, Nanostructures & Nanomaterials (Imperial College Press, 2004); Levinson, Principles of Lithography, Second Edition (SPIE Press, 2005); Doering and Nishi, Editors, Handbook of Semiconductor Manufacturing Technology, Second Edition (CRC Press, 2007); Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); Lakowicz, Principles of Fluorescence Spectroscopy, $3^{rd}$ edition (Springer, 2006); Hermanson, Bioconjugate Techniques, Second Edition (Academic Press, 2008); and the like, which relevant parts are hereby incorporated by reference.

The present invention is directed to methods and devices for optically-based nanopore analysis of molecules, such as nucleic acids, which comprise nanopore arrays with one or more light-blocking layers, that is, one or more opaque layers. Typically nanopore arrays are fabricated in thin sheets of material, such as, silicon, silicon nitride, silicon oxide, aluminum oxide, or the like, which readily transmit light, particularly at the thicknesses used, e.g. less than 50-100 nm. For electrical detection of analytes this is not a problem. However, in optically-based detection of labeled molecules translocating through nanopores, light transmitted through an array invariably excites materials outside of intended reaction sites, or signal generation regions, thereby generating optical noise, for example, from nonspecific background fluorescence, fluorescence from labels of molecules that have not yet entered a nanopore, or the like. In one aspect, the invention addresses this problem by providing nanopore arrays with one or more light-blocking layers that reflect and/or absorb light from an excitation beam, thereby reducing background noise for optical signals generated at intended reaction sites associated with nanopores of an array. In some embodiments, this permits optical labels in intended reaction sites (such as detection zones or signal generation zones described more fully below) to be excited by direct illumination. In some embodiments, an opaque layer may be a metal layer. Such metal layer may comprise Sn, Al, V, Ti, Ni, Mo, Ta, W, Au, Ag or Cu. In some embodiments such metal layer may comprise Al, Au, Ag or Cu. In still other embodiments, such metal layer may comprise aluminum or gold, or may comprise solely aluminum. The thickness of an opaque layer may vary widely and depends on the physical and chemical properties of material composing the layer. In some embodiments, the thickness of an opaque layer may be at least 5 nm, or at least 10 nm, or at least 40 nm. In other embodiments, the thickness of an opaque layer may be in the range of from 5-100 nm; in other embodiments, the thickness of an opaque layer may be in the range of from 10-80 nm. An opaque layer need not block (i.e. reflect or absorb) 100 percent of the light from an excitation beam. In some embodiments, an opaque layer may block at least 10 percent of incident light from an excitation beam; in other embodiments, an opaque layer may block at least 50 percent of incident light from an excitation beam.

FIG. 1A illustrates the above aspects of the invention for a particular embodiment. Solid state membrane (100) has opaque coating (102) on first side (104) to form layered membrane (101) with surface (105) facing first chamber (112) and with second side (106) facing second chamber (114). Layered membrane (101) separates first chamber (112) from second chamber (114) and comprises an array of apertures (110) that each provide fluid communication between first chamber (112) and second chamber (114). Apertures (110) may be solid state, or synthetic, nanopores, which may be used directly, or they may be used to immobilize protein nanopores, through which translocation take place. Generally, apertures have diameters, or cross sectional dimensions, that are less than the wavelength of an excitation beam, so that light from such beam is not transmitted through the apertures. In some embodiments, apertures have diameters of 100 nm or less. In some embodiments, the diameter of a circular aperture is 0.586 of the wavelength of the excitation beam or less.

In some embodiments of the preceding paragraph, a method of the invention may be implemented with the following steps: (a) providing a nanopore array comprising a solid phase membrane having a first side, a second side, and a plurality of apertures therethrough, wherein the solid phase membrane separates a first chamber and a second chamber such that each aperture provides fluid communication between the first chamber and the second chamber and wherein the first side of the solid phase membrane has an opaque coating thereon and each aperture has a detection region extending from the opaque coating of the first side toward the second side; (b) translocating polymers from the first chamber to the second chamber through the apertures, each polymer having one or more optical labels attached thereto capable of generating a signal having at least a first wavelength indicative of a characteristic of the polymer; (c) illuminating from the second side of the solid phase membrane the optical labels in the detection regions of the apertures with an excitation beam having a second wavelength so that optical labels in the detection regions generate signals whose first wavelength is different than the second wavelength; and (d) detecting signals from the optical labels in the detection regions to determine the characteristics of the polymers.

Figure 1B:
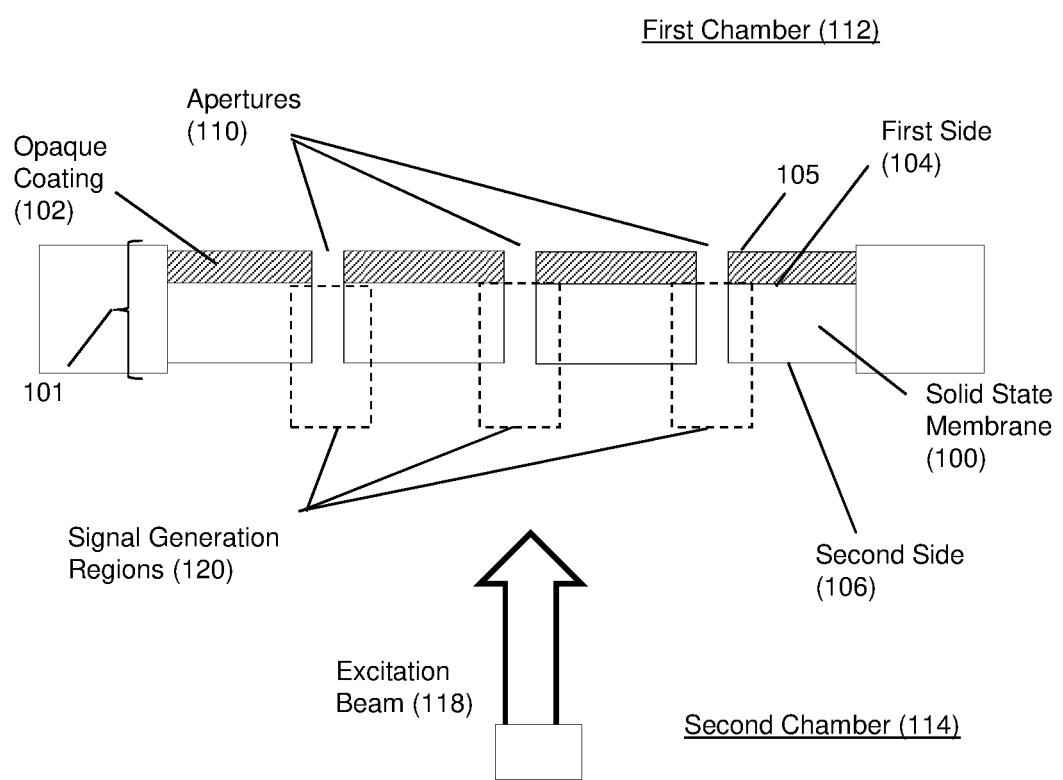
Figure 1C:
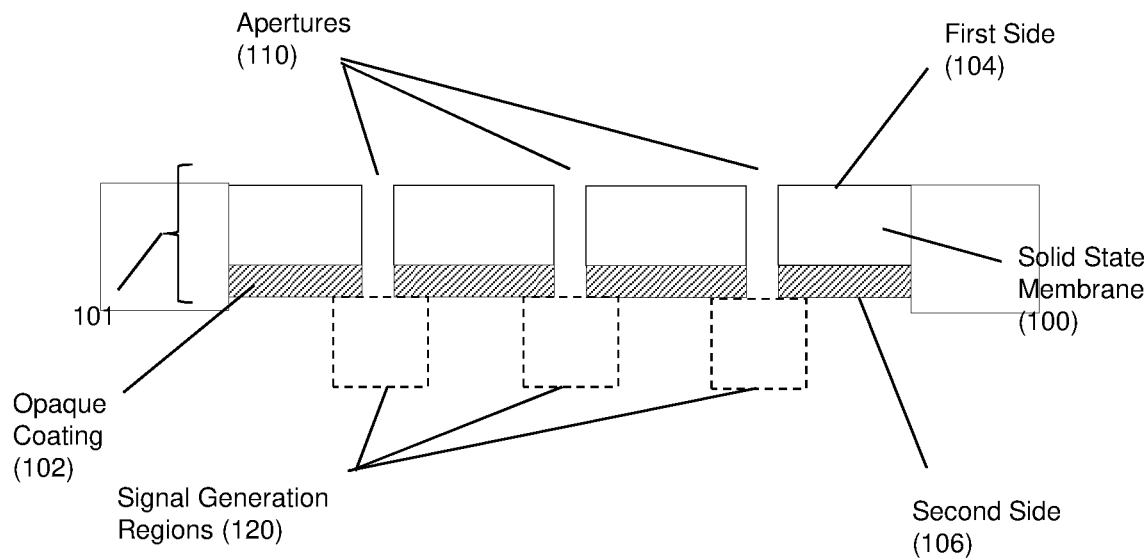
Figure 1C:
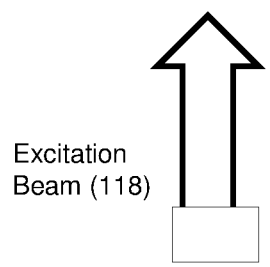

In other embodiments, as exemplified in FIG. 1C, methods of the invention may comprise the following steps: (a) providing a nanopore array comprising a solid phase membrane having a first side, a second side, and a plurality of apertures therethrough, wherein the solid phase membrane separates a first chamber and a second chamber such that each aperture provides fluid communication between the first chamber and the second chamber and wherein the second side of the solid phase membrane has an opaque coating thereon and each aperture has a detection region extending from the opaque coating of the second side into the second chamber; (b) translocating polymers from the first chamber to the second chamber through the apertures, each polymer having one or more optical labels attached thereto capable of generating a signal having at least a first wavelength indicative of a characteristic of the polymer; (c) illuminating from the second side of the solid phase membrane the optical labels in the detection regions of the apertures with an excitation beam having a second wavelength so that optical labels in the detection regions generate signals whose first wavelength is different than the second wavelength; and (d) detecting signals from the optical labels in the detection regions to determine the characteristics of the polymers.

In some embodiments, whenever the opaque coating or layer is a metal, a nearest-neighbor nanopore distance and excitation beam wavelength are selected to minimize plasmon-mediated extraordinary transmission through the nanopore array. Guidance for such selections are disclosed in the following references that are incorporated by reference: Ebbesen et al, Nature, 391: 667-669 (1998); Ebbesen et al, U.S. Pat. Nos. 5,973,316; 6,040,936; 6,236,033; 6,856,715; 7,057,151; 7,248,756; 8,174,696; Gur et al, Optics Comm., 284: 3509-3517 (2011); Ghaemi et al, Physical Review B, 58: 6779-6782 (1998); Pacifici et al, Optics Express, 16(12): 9222-9238 (2008); and the like. In some embodiments, a nearest-neighbor nanopore distance (or expected nearest-neighbor nanopore distance, for example, in a random (e.g. Poisson distributed) array of nanopores) is selected which approximately equals an excitation wavelength, for example, for exciting optical labels.

In some embodiments, signal generation regions (116) (or equivalently, intended reaction sites) each include the interior of a nanopore and a region immediately adjacent to its exit on second side (106), wherein such region does not overlap the equivalent regions of other nanopores. In some embodiments, labeled molecules, such as labeled nucleic acid molecules, are loaded, or deposited, in first chamber (112) and are translocated through apertures of layered membrane (101) from first chamber (112) to second chamber (114), either directly or via an inserted protein nanopores. As labeled molecules transit apertures (110) and/or exit apertures (110) they may be directly illuminated with excitation beam (118). Excitation beam (118) may be selected or configured to directly excite the labeled molecules or to indirectly excite the labeled molecules via a FRET interaction. In some embodiments (FIG. 1B), signal generation regions (120) (or equivalently, intended reaction sites) each include the interior of a nanopore from first side (104) to second side (106) and a region immediately adjacent to its exit on second side (106), wherein such region does not overlap the equivalent regions of other apertures (or nanopores). In still other embodiments, signal generation regions (or intended reaction sites) each include the interior of a nanopore from its entrance from a first chamber to its exit at a second chamber and regions immediately adjacent to its entrance and its exit, wherein such regions do not overlap the equivalent regions of other apertures.

Figure 1D:
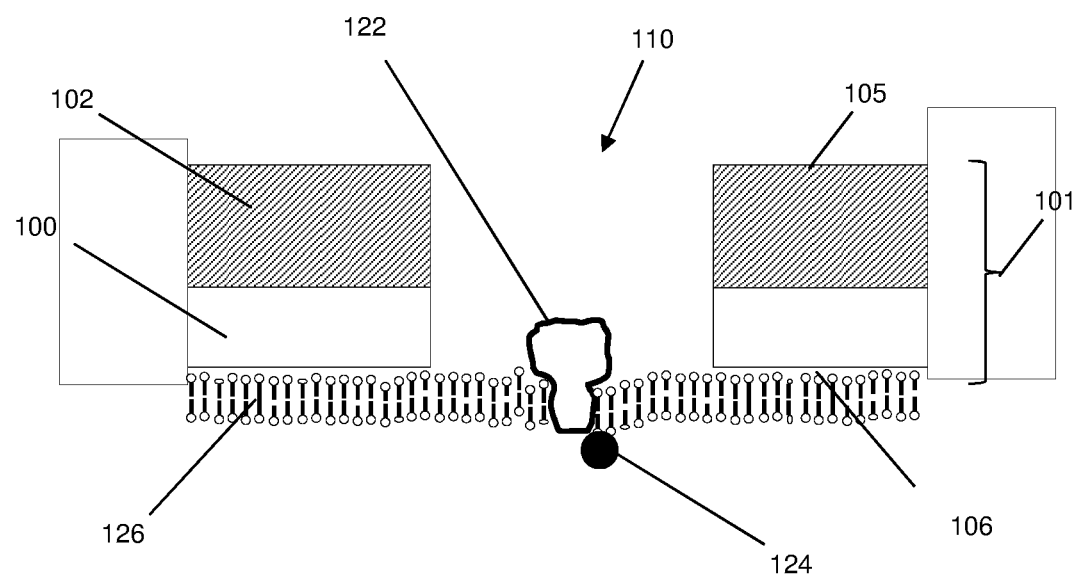
Figure 1E:
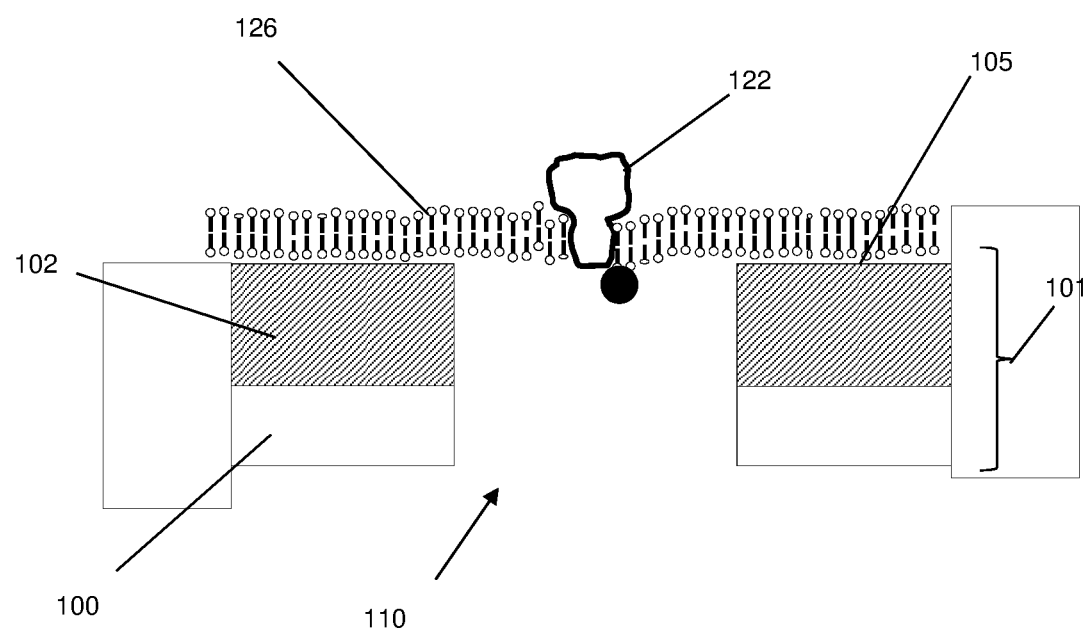

As mentioned above, apertures in layered membranes of the invention may be employed as nanopores directly or they may be used to hold, or immobilize, one or more protein nanopores. In some embodiments of the latter type, one or more protein nanopores may be embedded in a lipid bilayer disposed either on a surface of the opaque layer (e.g. 105 in FIG. 1A, 1B, or 1E) or on a surface of the second side of the layered membrane (e.g. 106 in FIG. 1D). In FIGS. 1D and 1E a section of a layered membrane (101) is shown with opaque layer or coating (102), solid state membrane (100), aperture (110), together with lipid bilayer (126) (which is shown on surface (106) in FIG. 1D and on surface (105) in FIG. 1E). In the particular embodiment shown, protein nanopore (122) that has label (124) attached (e.g. a donor label, such as a quantum dot, metal nanoparticle, or other fluorescent nanoparticle for generating FRET signals) is shown inserted into lipid bilayer (126), although as noted elsewhere, the invention comprehends protein nanopores in such configurations without labels for FRET signal generation. Some embodiments of FIG. 1D which have a signal generation region adjacent to label (124) (that is, within a FRET distance of label (124)) correspond to the configuration described in FIG. 1B in which signal generation regions extend from first side (104) to a space proximal to the aperture or nanopore exit at second side (106). Similarly, some embodiments of FIG. 1E which also have a signal generation region adjacent to label (124) (for example, within a FRET distance of label (124)) correspond to the configuration described in FIG. 1A in which signal generation regions extend from surface (105) to a space proximal to the aperture or nanopore exits at second side (106).

In some embodiments, such as those described in FIGS. 1A-1E, the layered membrane may further comprise a passivation coating, such as an oxide coating, such as a silicon oxide coating, to stabilize metal layers. For example, a silicon nitride membrane may be coated with an opaque material, such as a metal, using physical or chemical deposition techniques to form a layered membrane, after which apertures may be etched or drilled using a focused electron or ion beam to form an array of apertures in the layered membrane. Such array may then be further coated with protecting layer, such as silicon oxide, again using chemical or vapor deposition techniques.

In some embodiments, the invention may include a method for characterizing polymers, such as biological polymers including nucleic acids and proteins, by the following steps: (a) providing a nanopore array comprising a solid phase membrane having a first side, a second side, and a plurality of apertures therethrough, wherein the solid phase membrane separates a first chamber and a second chamber such that each aperture provides fluid communication between the first chamber and the second chamber and wherein the first side of the solid phase membrane has an opaque coating thereon and each aperture has a detection region extending from the opaque coating of the first side toward the second side; (b) translocating polymers from the first chamber to the second chamber through the apertures, each polymer having one or more optical labels attached thereto capable of generating a signal having at least a first wavelength indicative of a characteristic of the polymer; (c) illuminating from the second side of the solid phase membrane the optical labels in the detection regions of the apertures with an excitation beam comprising at least a second wavelength so that optical labels in the detection regions generate signals whose first wavelength is different than the second wavelength; (d) detecting signals from the optical labels in the detection regions to determine the characteristics of the polymers. In some embodiments, polymers may be polynucleotides or proteins. In still other embodiments, polymers may be polynucleotides. In further embodiments, polynucleotides may be single stranded nucleic acids. In some embodiments, a characteristic of polymers analyzed or determined is a monomer sequence, such as a nucleotide sequence, of the polymers. In some embodiments, optical labels on polymers are FRET labels, such as described in U.S. patents and patent and international publications: U.S. Pat. No. 8,771,491; US2013/0203050; or WO2014/190322, which are incorporated herein by reference. In some embodiments, apertures comprise protein nanopores. Briefly, in some embodiments, a FRET label comprises at each signal generation region at least one FRET donor label and at least one FRET acceptor label, wherein an excitation beam excites the FRET donor labels which, in turn, transfer energy to FRET acceptor labels within a FRET distance of the donor labels which, in turn, emit an optical signal. Typically, an excitation beam comprises a second wavelength and the optical signal comprises a first wavelength distinct from the second wavelength, for example, to permit use of an epi-illumination system. In some embodiments, a detection region may extend from the opaque coating of the first side toward the second side and include an extra-membrane space immediately proximal to the exit of an aperture and/or nanopore. In some embodiments, such extra-membrane space does not extend beyond 50 nm from the exit of a nanopore or aperture; in other embodiments, such extra-membrane space does not extend beyond 10 nm from the exit of a nanopore or aperture.

Briefly, as described more fully in U.S. Pat. No. 8,771,491, in some embodiments, an aperture and/or nanopore may be labeled with one or more FRET donors and polymers may each be labeled with FRET acceptors such that at least selected donors and acceptors form FRET pairs; that is, the emission spectra of a donor overlaps the absorption spectra of at least one acceptor so that if other conditions are met (e.g. donor excitation, donor and acceptor being within a FRET distance, donor and acceptor having proper relative orientation, and the like) a FRET interaction can occur. In a FRET interaction excitation energy of the donor is transferred to an acceptor non-radiatively, after which the acceptor, emits an optical signal that has a lower energy than the excitation energy of the donor. Donor are usually excited by illuminating them with a light beam, such as generated by a laser.

Figure 1F:
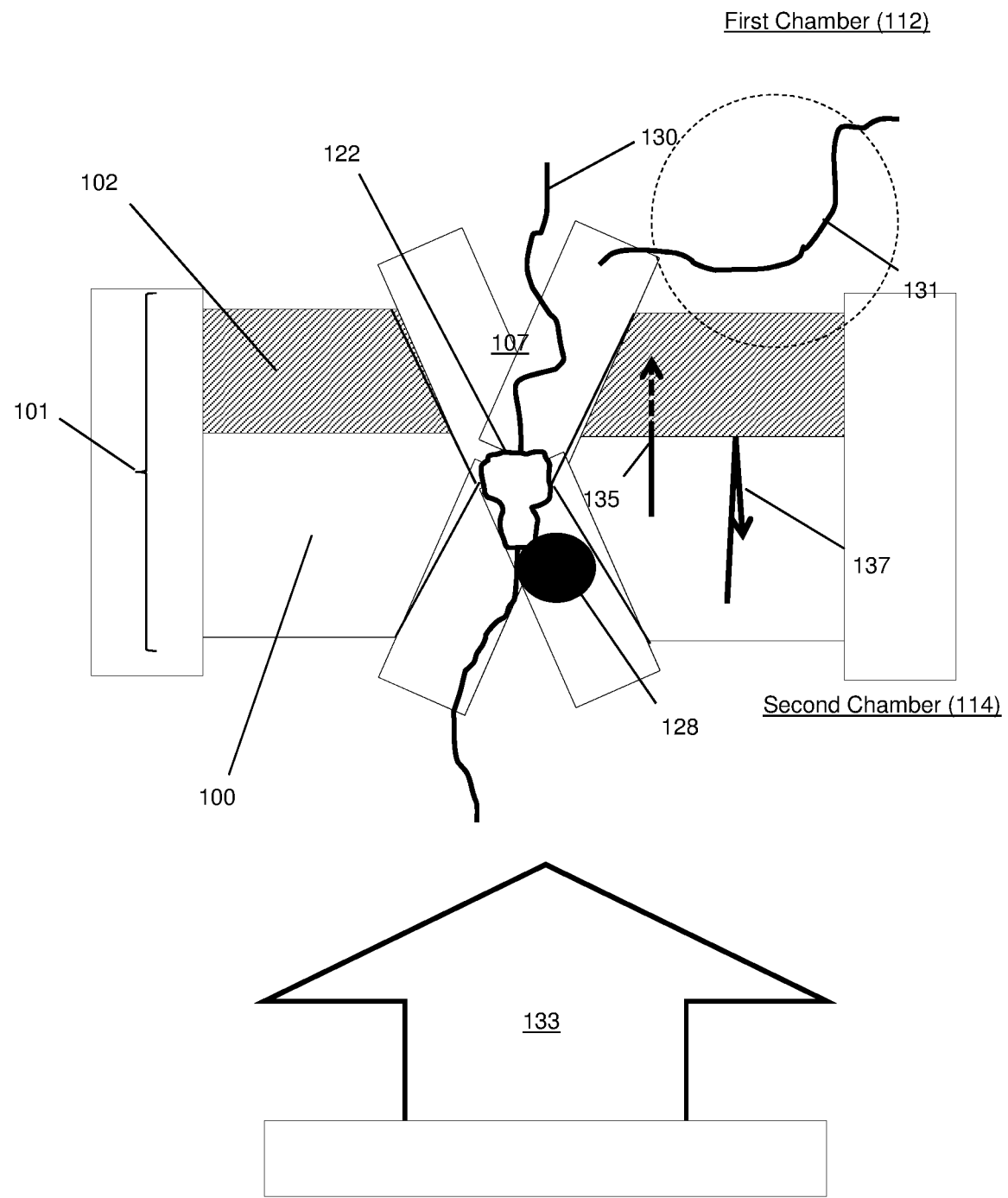

In some embodiments, protein nanopores may be inserted in solid state membranes without, or with only small amounts of, lipid bilayers to form arrays, as described in Huber et al, U.S. patent publication 2013/0203050, which is incorporated herein by reference. Such a protein nanopore/aperture configuration is illustrated in FIG. 1F. In this particular embodiment, layered membrane (101) comprising solid state membrane (100) and opaque layer (102) comprises aperture (107) having immobilized therein protein nanopore (122) labeled with donor (128), which may be an optically active particle, such as a quantum dot. As acceptor labeled polymer (130) passes through and exits bore of protein nanopore (122), acceptor labels pass within a FRET distance of donor (128). The size of aperture (107) is fabricated to be capable of immobilizing a single protein nanopore. Upon direct illumination of aperture (107) by excitation beam (133), donor (128) is excited and made capable of entering a FRET interaction with an acceptor of labeled polymer (130) being translocated through protein nanopore (122). On the other hand, opaque layer (102) decreases radiation from beam (133) from illuminating acceptors on labeled polymer (131) which is located on the opposite side of opaque layer (102) as beam (133). Opaque layer (102) blocks radiation from beam (133) by either absorbing (135) and/or reflecting (137) it.

Figure 1G:
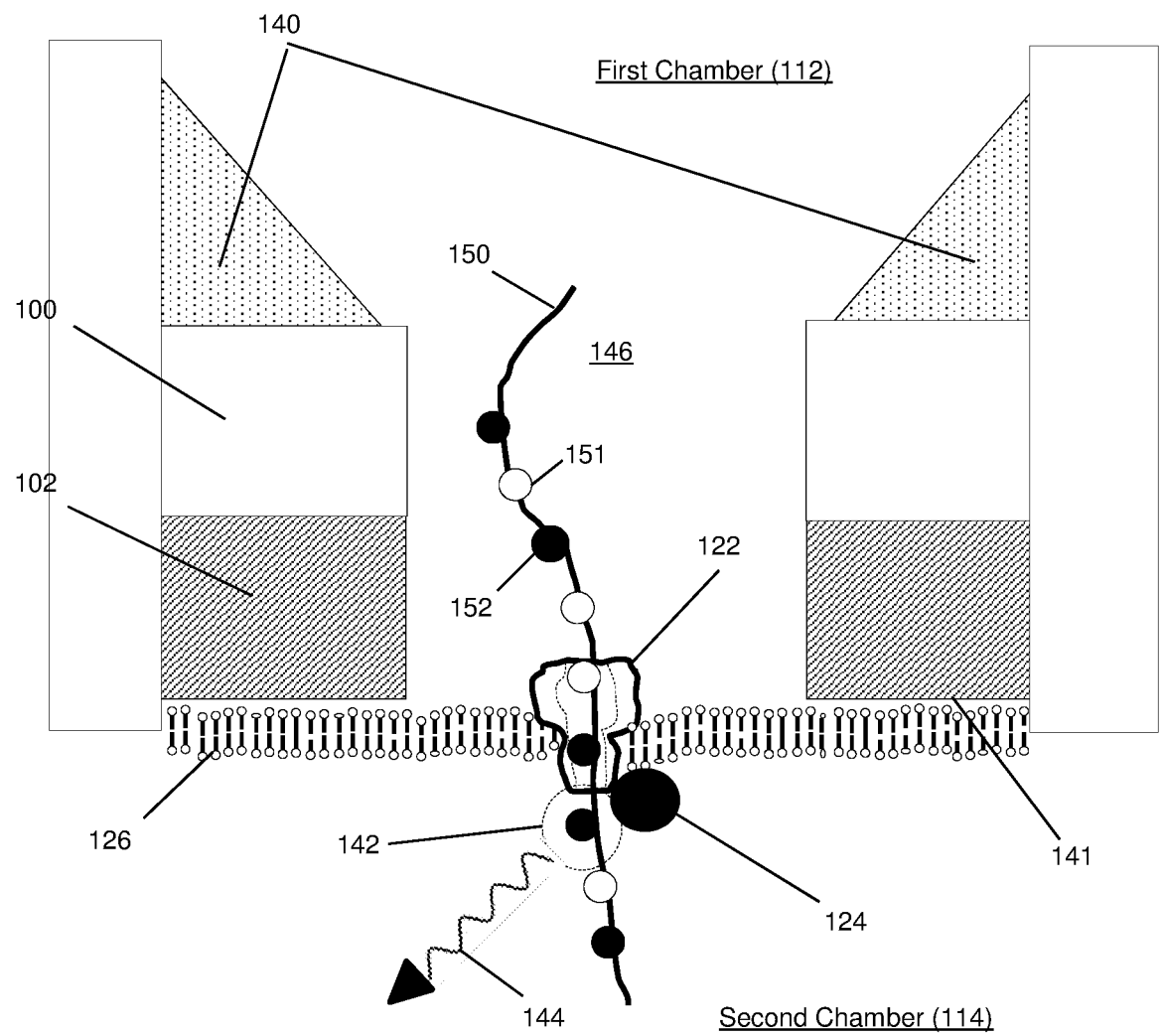

A further embodiment is illustrated in FIG. 1G in which a surface of opaque layer (102), such as a metal layer, forms a boundary of second chamber (114). In some embodiments, arrays of solid state apertures (146) may be fabricated using conventional micromachining techniques. For example, to a silicon substrate (140), nonconductive solid state membrane (100), such as a silicon nitride layer, is added, for example by chemical vapor deposition, or like technique. In some embodiments, layer (100) is in the range of 30-100 nm. On top of layer (100), opaque layer (102), such as a metal layer, is added, for example, by chemical vapor deposition or like technique to form a three-layer sheet. To opaque layer (102) a layer of photoresist may be added, which after removing developed photoresist material at aperture locations, holes are formed by etching through opaque layer (102) and solid state membrane (100), to form a portion of aperture (146). A second etching is carried out through silicon layer (140) to form the rest of apertures (146) in the array. A nanopore sensing device in accordance with one embodiment of the invention may be constructed by disposing lipid bilayer (126) on surface (141) of opaque layer (102), which has inserted therein at least one protein nanopore (122) with FRET donor label (124). Upon diposition in first chamber (112) charged and labeled polymer (150), for example comprising acceptor labels (151) and (152) for two different kinds of monomers, may translocate through protein nanopore (122) which constrains each acceptor label (151 or 152) to come within a FRET distance (142) of donor label (124). Donor label (124) is excited by beam (133) and transfers excitation energy to acceptor labels within FRET distance (142), which, in turn, emit FRET signal (144) indicative of the monomer to which it is attached.

Figure 1H:
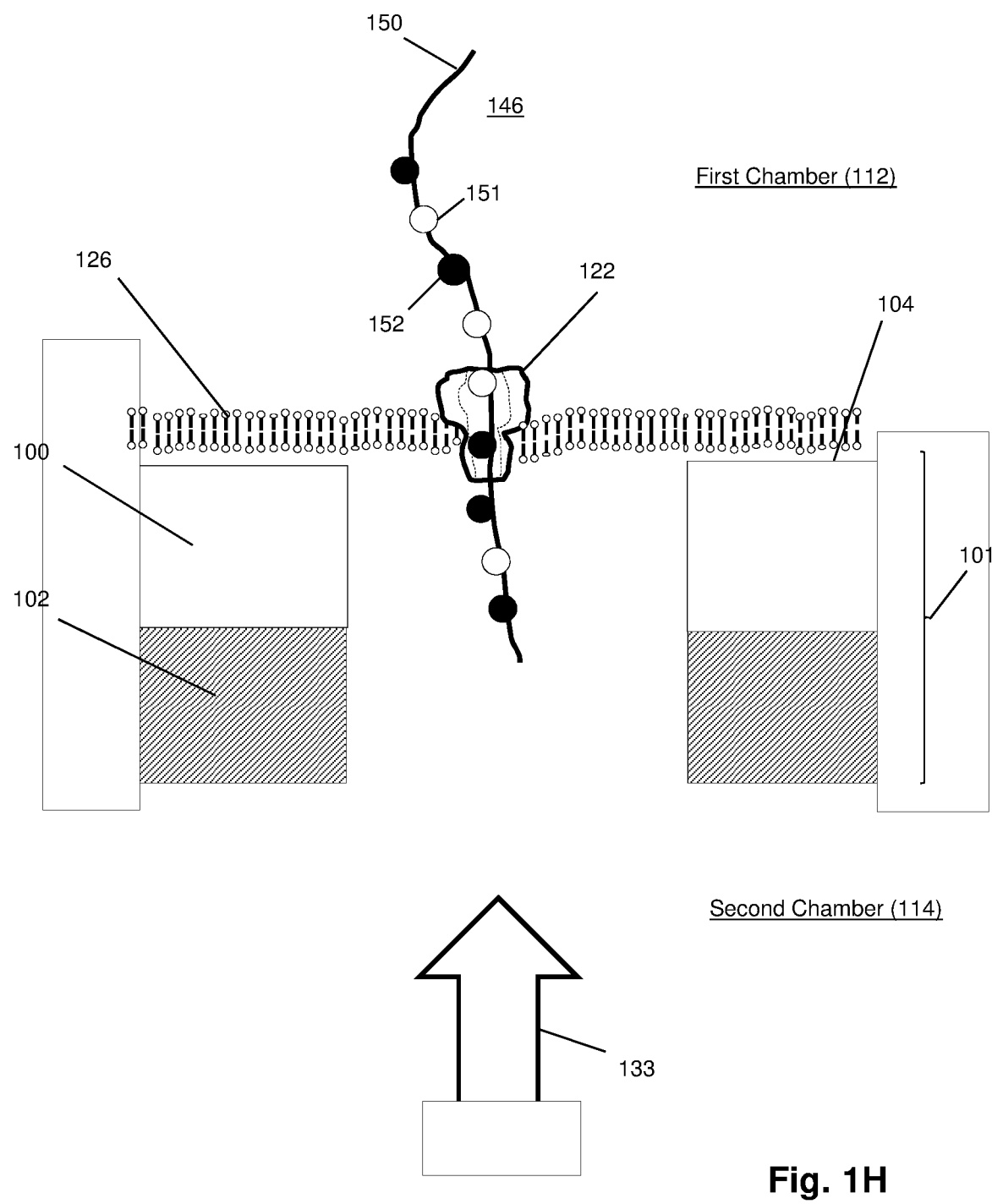

In still other embodiments, as illustrated in FIG. 1H, lipid bilayer (126) may be disposed on surface (104) of layer (100), so that protein nanopore (122) is inserted on a side of layered membrane (101) opposite from the side to which excitation beam (133) is directed.

Figure 2A:
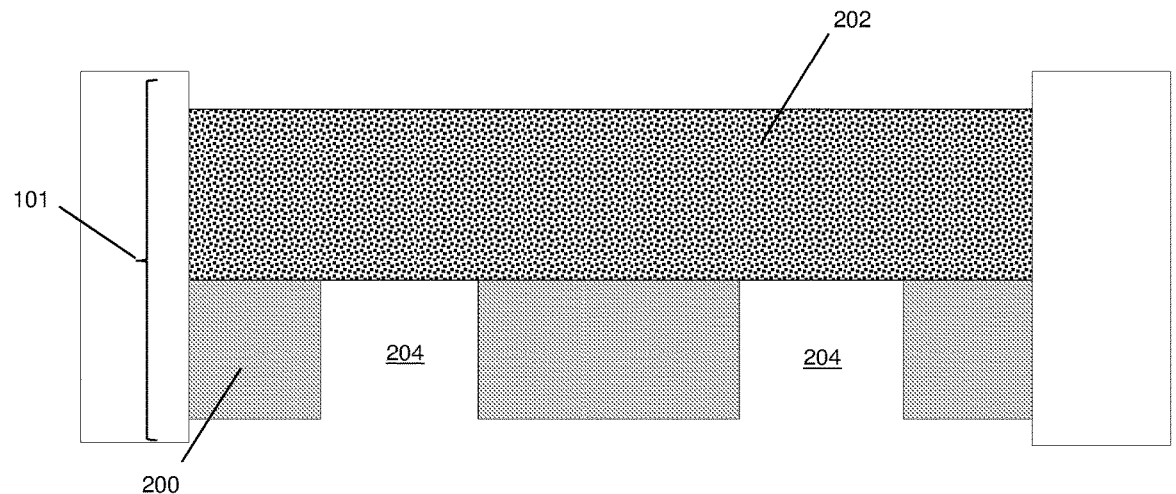
FIGS. 2A-2B illustrate an embodiment employing a porous layer as an opaque layer.
Figure 2B:
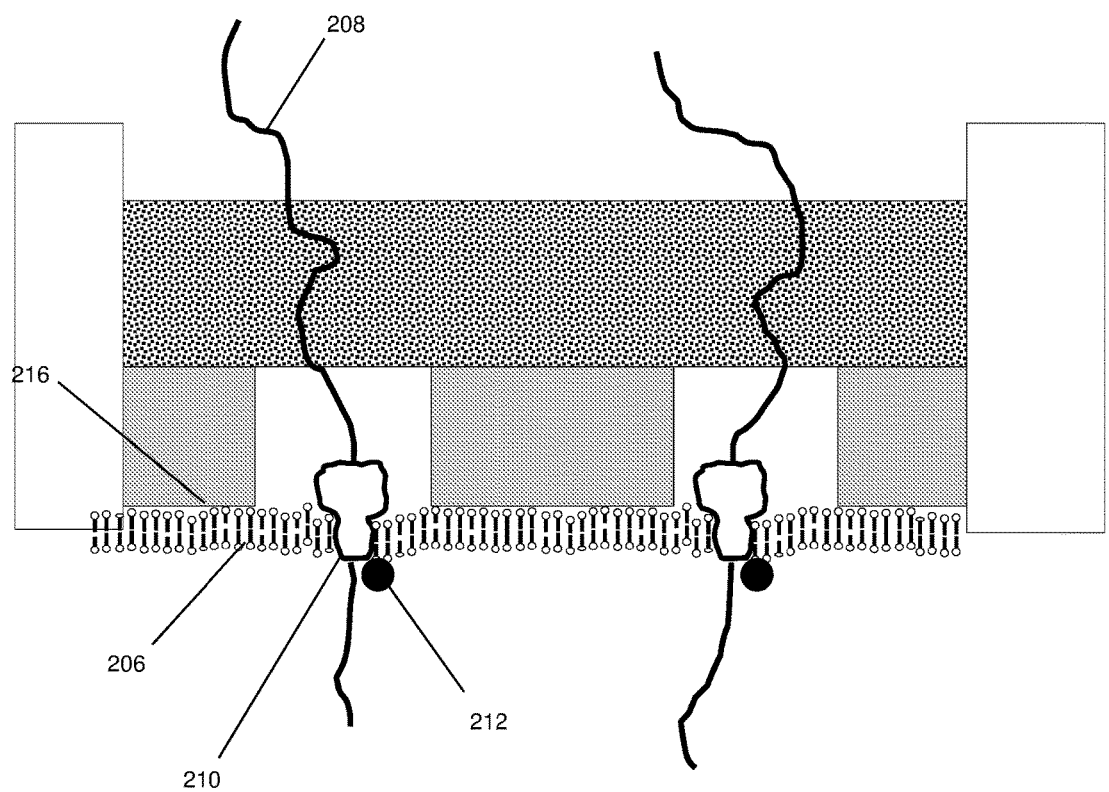

In some embodiments, an opaque layer may comprise an opaque porous layer, which in some embodiments may be an opaque nanoporous layer, as illustrated in FIGS. 2A and 2B. In such embodiments, layered membrane (101) comprises solid state membrane (200) and nanoporous layer (202) which comprises an opaque material having nanometer-sized pores that provide indirect and/or serpentine passages across the layer to apertures (204). FIG. 2B illustrates an embodiment with labeled protein nanopores (210) inserted in lipid bilayer (206) disposed on second side (216) of solid state membrane (200). As with the embodiments of FIGS. 1A-1H, nanoporous layer (202) blocks or reduces radiation directed to second side (216) of solid state membrane (200) from reaching labeled polymers or other materials on the other side of nanoporous layer (202), thereby reducing the generation of undesirable noise in optical signals from detection events at the exit of protein nanopore (210).

Figure 3:
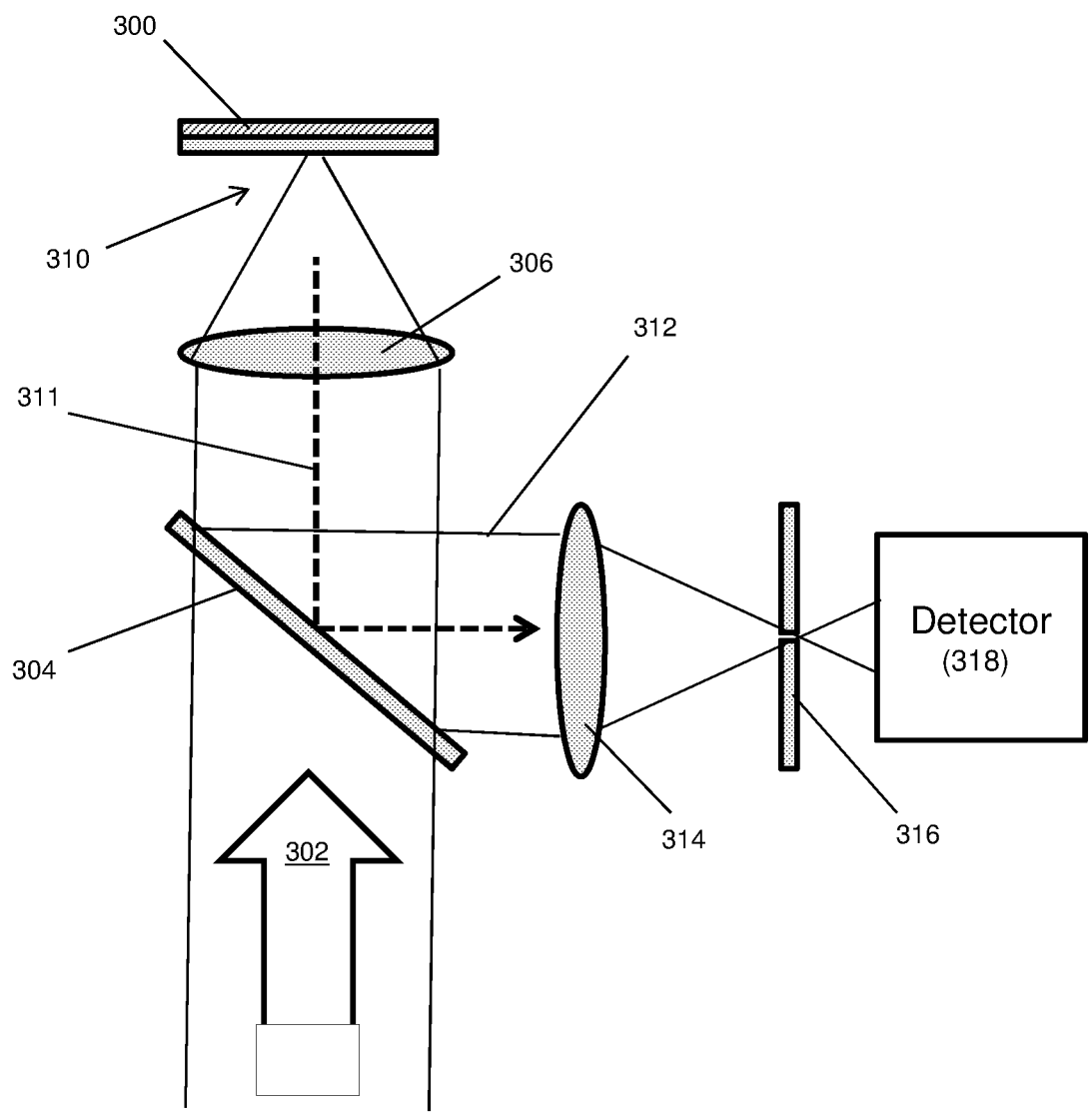
FIG. 3 illustrates the basic components of a confocal epi-illumination system.

As mentioned above, in some embodiments, an epi-illumination system, in which excitation beam delivery and optical signal collection occurs through a single objective, may be used for direct illumination of labels on a polymer analyte or donors on nanopores. The basic components of a confocal epi-illumination system for use with the invention is illustrated in FIG. 3. Excitation beam (302) passes through dichroic (304) and onto objective lens (306) which focuses (310) excitation beam (302) onto layered membrane (300), in which labels are excited directly to emit an optical signal, such as a fluorescent signal, of are excited indirectly via a FRET interaction to emit an optical signal. Such optical signal is collected by objective lens (306) and directed to dichroic (304), which is selected so that it passes light of excitation beam (302) but reflects light of optical signals (311). Reflected optical signals (311) passes through lens (314) which focuses it through pinhole (316) and onto detector (318).

In some embodiments, a device for implementing the above method for polymers comprising single stranded nucleic acids typically includes a set of electrodes for establishing an electric field across the layered membrane and nanopores. Single stranded nucleic acids are exposed to nanopores by placing them in an electrolyte in a first chamber, which is configured as the "cis" side of the layered membrane by placement of a negative electrode in the chamber. Upon application of an electric field, the negatively single stranded nucleic acids are captured by nanopores and translocated to a second chamber on the other side of the layered membrane, which is configured as the "trans" side of membrane by placement of a positive electrode in the chamber. The speed of translocation depends in part on the ionic strength of the electrolytes in the first and second chambers and the applied voltage across the nanopores. In optically based detection, a translocation speed may be selected by preliminary calibration measurements, for example, using predetermined standards of labeled single stranded nucleic acids that generate signals at different expected rates per nanopore for different voltages. Thus, for DNA sequencing applications, a translocation speed may be selected based on the signal rates from such calibration measurements. Consequently, from such measurements a voltage may be selected that permits, or maximizes, reliable nucleotide identifications, for example, over an array of nanopores. In some embodiments, such calibrations may be made using nucleic acids from the sample of templates being analyzed (instead of, or in addition to, predetermined standard sequences). In some embodiments, such calibrations may be carried out in real time during a sequencing run and the applied voltage may be modified in real time based on such measurements, for example, to maximize the acquisition of nucleotide-specific signals.

Nanopores and Nanopore Arrays

As discussed above, nanopores used with the invention may be solid-state nanopores, protein nanopores, or hybrid nanopores comprising protein nanopores or organic nanotubes such as carbon or graphene nanotubes, configured in a solid-state membrane, or like framework. Important features of nanopores include constraining polymer analytes, such as polynucleotides, so that their monomers pass through a detection zone (or signal generation region) in sequence (that is, so that nucleotides pass a detection zone one at a time, or in single file). In some embodiments, additional features of nanopores include passing single stranded nucleic acids while not passing double stranded nucleic acids, or equivalently bulky molecules.

In some embodiments, nanopores used in connection with the methods and devices of the invention are provided in the form of arrays, such as an array of clusters of nanopores, which may be disposed regularly on a planar surface. In some embodiments, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Solid state nanopores may be fabricated in a variety of materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Ling, U.S. Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503; Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004); Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like.

In some embodiments, the invention comprises nanopore arrays with one or more light-blocking layers, that is, one or more opaque layers. Typically nanopore arrays are fabricated in thin sheets of material, such as, silicon, silicon nitride, silicon oxide, aluminum oxide, or the like, which readily transmit light, particularly at the thicknesses used, e.g. less than 50-100 nm. For electrical detection of analytes this is not a problem. However, in optically-based detection of labeled molecules translocating nanopores, light transmitted through an array invariably excites materials outside of intended reaction sites, thus generates optical noise, for example, from nonspecific background fluorescence, fluorescence from labels of molecules that have not yet entered a nanopore, or the like. In one aspect, the invention addresses this problem by providing nanopore arrays with one or more light-blocking layers that reflect and/or absorb light from an excitation beam, thereby reducing background noise for optical signals generated at intended reaction sites associated with nanopores of an array. In some embodiments, this permits optical labels in intended reaction sites to be excited by direct illumination. In some embodiments, an opaque layer may be a metal layer. Such metal layer may comprise Sn, Al, V, Ti, Ni, Mo, Ta, W, Au, Ag or Cu. In some embodiments such metal layer may comprise Al, Au, Ag or Cu. In still other embodiments, such metal layer may comprise aluminum or gold, or may comprise solely aluminum. The thickness of an opaque layer may vary widely and depends on the physical and chemical properties of material composing the layer. In some embodiments, the thickness of an opaque layer may be at least 5 nm, or at least 10 nm, or at least 40 nm. In other embodiments, the thickness of an opaque layer may be in the range of from 5-100 nm; in other embodiments, the thickness of an opaque layer may be in the range of from 10-80 nm. An opaque layer need not block (i.e. reflect or absorb) 100 percent of the light from an excitation beam. In some embodiments, an opaque layer may block at least 10 percent of incident light from an excitation beam; in other embodiments, an opaque layer may block at least 50 percent of incident light from an excitation beam.

Opaque layers or coatings may be fabricated on solid state membranes by a variety of techniques known in the art. Material deposition techniques may be used including chemical vapor deposition, electrodeposition, epitaxy, thermal oxidation, physical vapor deposition, including evaporation and sputtering, casting, and the like. In some embodiments, atomic layer deposition may be used, e.g. U.S. Pat. No. 6,464,842; Wei et al, Small, 6(13): 1406-1414 (2010), which are incorporated by reference.

In some embodiments, a 1-100 nm channel or aperture may be formed through a solid substrate, usually a planar substrate, such as a membrane, through which an analyte, such as single stranded DNA, is induced to translocate. In other embodiments, a 2-50 nm channel or aperture is formed through a substrate; and in still other embodiments, a 2-30 nm, or a 2-20 nm, or a 3-30 nm, or a 3-20 nm, or a 3-10 nm channel or aperture if formed through a substrate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand provide reproducible narrow bores, or lumens, especially in the 1-10 nanometer range, as well as techniques for tailoring the physical and/or chemical properties of the nanopore and for directly or indirectly attaching groups or elements, such as fluorescent labels, which may be FRET donors or acceptors, by conventional protein engineering methods. Protein nanopores typically rely on delicate lipid bilayers for mechanical support, and the fabrication of solid-state nanopores with precise dimensions remains challenging. In some embodiments, solid-state nanopores may be combined with a biological nanopore to form a so-called "hybrid" nanopore that overcomes some of these shortcomings, thereby providing the precision of a biological pore protein with the stability of a solid state nanopore. For optical read out techniques a hybrid nanopore provides a precise location of the nanopore which simplifies the data acquisition greatly.

In some embodiments, clusters may also be formed by disposing protein nanopores in lipid bilayers supported by solid phase membrane containing an array of apertures. For example, such an array may comprise apertures fabricated (e.g. drilled, etched, or the like) in solid phase support. The geometry of such apertures may vary depending on the fabrication techniques employed. In some embodiments, each such aperture is associated with, or encompassed by, a separate resolution limited area; however, in other embodiments, multiple apertures may be within the same resolution limited area. The cross-sectional area of the apertures may vary widely and may or may not be the same as between different clusters, although such areas are usually substantially the same as a result of conventional fabrication approaches. In some embodiments, apertures have a minimal linear dimension (e.g. diameter in the case of circular apertures) in the range of from 10 to 200 nm, or have areas in the range of from about 100 to $3 \times 10^4$ nm$^2$. Across the apertures may be disposed a lipid bilayer. The distribution of protein nanopores per aperture may be varied, for example, by controlling the concentration of protein nanopores during inserting step. In such embodiments, clusters of nanopores may comprise a random number of nanopores. In some embodiments, in which protein nanopores insert randomly into apertures, clusters containing one or more apertures on average have a number of protein nanopores that is greater than zero; in other embodiments, such clusters have a number of protein nanopores that is greater than 0.25; in other embodiments, such clusters have a number of protein nanopores that is greater than 0.5; in other embodiments, such clusters have a number of protein nanopores that is greater than 0.75; in other embodiments, such clusters have a number of protein nanopores that is greater than 1.0.

In some embodiments, methods and devices of the invention comprise a solid phase membrane, such as a SiN membrane, having an array of apertures therethrough providing communication between a first chamber and a second chamber (also sometimes referred to as a "cis chamber" and a "trans chamber") and supporting a lipid bilayer on a surface facing the second, or trans, chamber. In some embodiments, diameters of the aperture in such a solid phase membrane may be in the range of 10 to 200 nm, or in the range of 20 to 100 nm. In some embodiments, such solid phase membranes further include protein nanopores inserted into the lipid bilayer in regions where such bilayer spans the apertures on the surface facing the trans chamber. In some embodiments, such protein nanopores are inserted from the cis side of the solid phase membrane using techniques described herein. In some embodiments, such protein nanopores have a structure identical to, or similar to, α-hemolysin in that it comprises a barrel, or bore, along an axis and at one end has a "cap" structure and at the other end has a "stem" structure (using the terminology from Song et al, Science, 274: 1859-1866 (1996)). In some embodiments using such protein nanopores, insertion into the lipid bilayer results in the protein nanopore being oriented so that its cap structure is exposed to the cis chamber and its stem structure is exposed to the trans chamber.

In some embodiments, the present invention may employ hybrid nanopores in clusters, particularly for optical-based nanopore sequencing of polynucleotides. Such nanopores comprise a solid-state orifice, or aperture, into which a protein biosensor, such as a protein nanopore, is stably inserted. A charged polymer may be attached to a protein nanopore (e.g. alpha hemolysin) by conventional protein engineering techniques after which an applied electric field may be used to guide a protein nanopore into an aperture in a solid-state membrane. In some embodiments, the aperture in the solid-state substrate is selected to be slightly smaller than the protein, thereby preventing it from translocating through the aperture. Instead, the protein will be embedded into the solid-state orifice.

In some embodiments, a donor fluorophore is attached to the protein nanopore. This complex is then inserted into a solid-state aperture or nanohole (for example, 3-10 nm in diameter) by applying an electric field across the solid state nanohole, or aperture, until the protein nanopore is transported into the solid-state nanohole to form a hybrid nanopore. The formation of the hybrid nanopore can be verified by (a) the inserted protein nanopore causing a drop in current based on a partial blockage of the solid-state nanohole and by (b) the optical detection of the donor fluorophore.

Solid state, or synthetic, nanopores may be preprared in a variety of ways, as exemplified in the references cited above. In some embodiments a helium ion microscope may be used to drill the synthetic nanopores in a variety of materials, e.g. as disclosed by Yang et al, Nanotechnolgy, 22: 285310 (2011), which is incorporated herein by reference. A chip that supports one or more regions of a thin-film material, e.g. silicon nitride, that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In some embodiments, a nanopore may have one or more labels attached for use in optically-based nanopore sequencing methods. The label may be a member of a Forster Resonance Energy Transfer (FRET) pair. Such labels may comprise organic fluorophores, chemiluminescent labels, quantum dots, metallic nanoparticles and/or fluorescent proteins. Target nucleic acids may have one distinct label per nucleotide. The labels attached to the nucleotides may be selected from the group consisting of organic fluorophores. The label attachment site in the pore protein can be generated by conventional protein engineering methods, e.g. a mutant protein can be constructed that will allow the specific binding of the label. As an example, a cysteine residue may be inserted at the desired position of the protein which inserts a thiol (SH) group that can be used to attach a label. The cysteine can either replace a natural occurring amino acid or can be incorporated as an addition amino acid. A maleimide-activated label is then covalently attached to the thiol residue of the protein nanopore. In a preferred embodiment the attachment of the label to the protein nanopore or the label on the nucleic acid is reversible. By implementing a cleavable crosslinker, an easily breakable chemical bond (e.g. an S—S bond or a pH labile bond) is introduced and the label may be removed when the corresponding conditions are met.

Optically Based Nanopore Sequencing with FRET Signals

In some embodiments, a nanopore may be labeled with one or more quantum dots. In particular, in some embodiments, one or more quantum dots may be attached to a nanopore, or attached to a solid phase support adjacent to (and within a FRET distance of an entrance or exit of a nanopore), and employed as donors in FRET reactions with acceptors on analytes. Such uses of quantum dots are well known and are described widely in the scientific and patent literature, such as, in U.S. Pat. Nos. 6,252,303; 6,855,551; 7,235,361; and the like, which are incorporated herein by reference.

One example of a Quantum dot which may be utilized as a pore label is a CdTe quantum dot which can be synthesized in an aqueous solution. A CdTe quantum dot may be functionalized with a nucleophilic group such as primary amines, thiols or functional groups such as carboxylic acids. A CdTe quantum dot may include a mercaptopropionic acid capping ligand, which has a carboxylic acid functional group that may be utilized to covalently link a quantum dot to a primary amine on the exterior of a protein pore. The cross-linking reaction may be accomplished using standard cross-linking reagents (homo-bifunctional as well as hetero-bifunctional) which are known to those having ordinary skill in the art of bioconjugation. Care may be taken to ensure that the modifications do not impair or substantially impair the translocation of a nucleic acid through the nanopore. This may be achieved by varying the length of the employed crosslinker molecule used to attach the donor label to the nanopore.

For example, the primary amine of the lysine residue 131 of the natural alpha hemolysin protein (Song, L. et al., Science 274, (1996): 1859-1866) may be used to covalently bind carboxy modified CdTe Quantum dots via 1-Ethyl-3-[3-dimethylaminopropyl]carbodiimide hydrochloride/N-hydroxysulfosuccinimide (EDC/NHS) coupling chemistry. Alternatively, amino acid 129 (threonine) may be exchanged into cysteine. Since there is no other cysteine residue in the natural alpha hemolysin protein the thiol side group of the newly inserted cysteine may be used to covalently attach other chemical moieties.

A biological polymer, e.g., a nucleic acid molecule or polymer, may be labeled with one or more acceptor labels. For a nucleic acid molecule, each of the four nucleotides or building blocks of a nucleic acid molecule may be labeled with an acceptor label thereby creating a labeled (e.g., fluorescent) counterpart to each naturally occurring nucleotide. The acceptor label may be in the form of an energy accepting molecule which can be attached to one or more nucleotides on a portion or on the entire strand of a converted nucleic acid.

A variety of methods may be utilized to label the monomers or nucleotides of a nucleic acid molecule or polymer. A labeled nucleotide may be incorporated into a nucleic acid during synthesis of a new nucleic acid using the original sample as a template ("labeling by synthesis"). For example, the labeling of nucleic acid may be achieved via PCR, whole genome amplification, rolling circle amplification, primer extension or the like or via various combinations and extensions of the above methods known to persons having ordinary skill in the art.

A label may comprise a reactive group such as a nucleophile (amines, thiols etc.). Such nucleophiles, which are not present in natural nucleic acids, can then be used to attach fluorescent labels via amine or thiol reactive chemistry such as NHS esters, maleimides, epoxy rings, isocyanates etc. Such nucleophile reactive fluorescent dyes (i.e. NHS-dyes) are readily commercially available from different sources. An advantage of labeling a nucleic acid with small nucleophiles lies in the high efficiency of incorporation of such labeled nucleotides when a "labeling by synthesis" approach is used. Bulky fluorescently labeled nucleic acid building blocks may be poorly incorporated by polymerases due to steric hindrance of the labels during the polymerization process into newly synthesized DNA.

Whenever two or more mutually quenching dyes are used, such dyes may be attached to DNA using orthogonal attachment chemistries. For example, NHS esters can be used to react very specifically with primary amines or maleimides will react with thiol groups. Either primary amines ($NH_2$) or thiol (SH) modified nucleotides are commercially available. These relatively small modifications are readily incorporated in a polymerase mediated DNA synthesis and can be used for subsequent labeling reactions using either NHS or maleimide modified dyes. Guidance for selecting and using such orthogonal linker chemistries may be found in Hermanson (cited above).

Additional orthogonal attachment chemistries for typical attachment positions include Huisgen-type cycloaddition for a copper-catalyzed reaction and an uncatalyzed reaction; alkene plus nitrile oxide cycloaddition, e.g. as disclosed in Gutsmiedl et al, Org. Lett., 11: 2405-2408 (2009); Diels-Alder cycloaddition, e.g. disclosed in Seelig et al, Tetrahedron Lett., 38: 7729-7732 (1997); carbonyl ligation, e.g. as disclosed in Casi et al, J. Am. Chem. Soc., 134: 5887-5892 (2012); Shao et al J. Am. Chem. Soc., 117: 3893-3899 (1995); Rideout, Science, 233: 561-563 (1986); Michael addition, e.g. disclosed in Brinkley, Bioconjugate Chemistry, 3: 2-13 (1992); native chemical ligation, e.g. disclosed in Schuler et al, Bioconjugate Chemistry, 13: 1039-1043 (2002); Dawson et al, Science, 266: 776-779 (1994); or amide formation via an active ester, e.g. disclosed in Hermanson (cited above).

A combination of 1, 2, 3 or 4 nucleotides in a nucleic acid strand may be exchanged with their labeled counterpart. The various combinations of labeled nucleotides can be sequenced in parallel, e.g., labeling a source nucleic acid or DNA with combinations of 2 labeled nucleotides in addition to the four single labeled samples, which will result in a total of 10 differently labeled sample nucleic acid molecules or DNAs (G, A, T, C, GA, GT, GC, AT, AC, TC). The resulting sequence pattern may allow for a more accurate sequence alignment due to overlapping nucleotide positions in the redundant sequence read-out. In some embodiments, a polymer, such as a polynucleotide or polypeptide, may be labeled with a single fluorescent label attached to a single kind of monomer, for example, every T (or substantially every T) of a polynucleotide is labeled with a fluorescent label, e.g. a cyanine dye. In such embodiments, a collection, or sequence, of fluorescent signals from the polymer may form a signature or fingerprint for the particular polymer. In some such embodiments, such fingerprints may or may not provide enough information for a sequence of monomers to be determined.

In some embodiments, a feature of the invention is the labeling of substantially all monomers of a polymer analyte with fluorescent dyes or labels that are members of a mutually quenching set. The use of the term "substantially all" in reference to labeling polymer analytes is to acknowledge that chemical and enzymatic labeling techniques are typically less than 100 percent efficient. In some embodiments, "substantially all" means at least 80 percent of all monomer have fluorescent labels attached. In other embodiments, "substantially all" means at least 90 percent of all monomer have fluorescent labels attached. In other embodiments, "substantially all" means at least 95 percent of all monomer have fluorescent labels attached.

A method for sequencing a polymer, such as a nucleic acid molecule includes providing a nanopore or pore protein (or a synthetic pore) inserted in a membrane or membrane like structure or other substrate. The base or other portion of the pore may be modified with one or more pore labels. The base may refer to the Trans side of the pore. Optionally, the Cis and/or Trans side of the pore may be modified with one or more pore labels. Nucleic acid polymers to be analyzed or sequenced may be used as a template for producing a labeled version of the nucleic acid polymer, in which one of the four nucleotides or up to all four nucleotides in the resulting polymer is/are replaced with the nucleotide's labeled analogue(s). An electric field is applied to the nanopore which forces the labeled nucleic acid polymer through the nanopore, while an external monochromatic or other light source may be used to illuminate the nanopore, thereby exciting the pore label. As, after or before labeled nucleotides of the nucleic acid pass through, exit or enter the nanopore, energy is transferred from the pore label to a nucleotide label, which results in emission of lower energy radiation. The nucleotide label radiation is then detected by a confocal microscope setup or other optical detection system or light microscopy system capable of single molecule detection known to people having ordinary skill in the art. Examples of such detection systems include but are not limited to confocal microscopy, epi-illumination fluorescence microscopy, and the like. In some embodiments, epi-illumination fluorescence microscopy is employed.

Energy may be transferred from a pore or nanopore donor label (e.g., a Quantum Dot) to an acceptor label on a polymer (e.g., a nucleic acid) when an acceptor label of an acceptor labeled monomer (e.g., nucleotide) of the polymer interacts with the donor label as, after or before the labeled monomer exits, enters or passes through a nanopore. For example, the donor label may be positioned on or attached to the nanopore on the cis or trans side or surface of the nanopore such that the interaction or energy transfer between the donor label and acceptor label does not take place until the labeled monomer exits the nanopore and comes into the vicinity or proximity of the donor label outside of the nanopore channel or opening. As a result, interaction between the labels, energy transfer from the donor label to the acceptor label, emission of energy from the acceptor label and/or measurement or detection of an emission of energy from the acceptor label may take place outside of the passage, channel or opening running through the nanopore, e.g., within a cis or trans chamber on the cis or trans sides of a nanopore. The measurement or detection of the energy emitted from the acceptor label of a monomer may be utilized to identify the monomer.

The nanopore label may be positioned outside of the passage, channel or opening of the nanopore such that the label may be visible or exposed to facilitate excitation or illumination of the label. The interaction and energy transfer between a donor label and accepter label and the emission of energy from the acceptor label as a result of the energy transfer may take place outside of the passage, channel or opening of the nanopore. This may facilitate ease and accuracy of the detection or measurement of energy or light emission from the acceptor label, e.g., via an optical detection or measurement device.

A donor label may be attached in various manners and/or at various sites on a nanopore. For example, a donor label may be directly or indirectly attached or connected to a portion or unit of the nanopore. Alternatively, a donor label may be positioned adjacent to a nanopore.

Each acceptor labeled monomer (e.g., nucleotide) of a polymer (e.g., nucleic acid) can interact sequentially with a donor label positioned on or next to or attached directly or indirectly to the exit of a nanopore or channel through which the polymer is translocated. The interaction between the donor and acceptor labels may take place outside of the nanopore channel or opening, e.g., after the acceptor labeled monomer exits the nanopore or before the monomer enters the nanopore. The interaction may take place within or partially within the nanopore channel or opening, e.g., while the acceptor labeled monomer passes through, enters or exits the nanopore.

When one of the four nucleotides of a nucleic acid is labeled, the time dependent signal arising from the single nucleotide label emission is converted into a sequence corresponding to the positions of the labeled nucleotide in the nucleic acid sequence. The process is then repeated for each of the four nucleotides in separate samples and the four partial sequences are then aligned to assemble an entire nucleic acid sequence.

When multi-color labeled nucleic acid (DNA) sequences are analyzed, the energy transfer from one or more donor labels to each of the four distinct acceptor labels that may exist on a nucleic acid molecule may result in light emission at four distinct wavelengths or colors (each associated with one of the four nucleotides) which allows for a direct sequence read-out.

A donor label (also sometimes referred to herein as a "pore label") may be placed as close as possible to the aperture (for example, at the exit) of a nanopore without causing an occlusion that impairs translocation of a nucleic acid through the nanopore. A pore label may have a variety of suitable properties and/or characteristics. For example, a pore label may have energy absorption properties meeting particular requirements. A pore label may have a large radiation energy absorption cross-section, ranging, for example, from about 0 to 1000 nm or from about 200 to 500 nm. A pore label may absorb radiation within a specific energy range that is higher than the energy absorption of the nucleic acid label, such as an acceptor label. The absorption energy of the pore label may be tuned with respect to the absorption energy of a nucleic acid label in order to control the distance at which energy transfer may occur between the two labels. A pore label may be stable and functional for at least 106 to 109 excitation and energy transfer cycles.

In some embodiments, a device for analyzing polymers each having optical labels attached to a sequence of monomers may comprise the following elements: (a) a nanopore array in a solid phase membrane separating a first chamber and a second chamber, wherein nanopores of the nanopore array each provide fluid communication between the first chamber and the second chamber and are arranged in clusters such that each different cluster of nanopores is disposed within a different resolution limited area and such that each cluster comprises a number of nanopores that is either greater than one or is a random variable with an average value greater than zero; (b) a polymer translocating system for moving polymers in the first chamber to the second chamber through the nanopores of the nanopore array; and (c) a detection system for collecting optical signals generated by optical labels attached to polymers whenever an optical label exits a nanopore within a resolution limited area.

Optically Based Nanopore Sequencing with Self-Quenching Dyes and/or Quenching Agents In one aspect, the invention includes the using nanopore arrays with opaque layers and direct illumination of fluorescently labeled polynucleotides for sequence determination. In some embodiments, such applications includes the use of fluorescent quenching, and fluorescent signaling to sequentially identify nucleotides of fluorescently labeled polynucleotide analytes. Such analysis of polynucleotide analytes may be carried out on pluralities of polynucleotides in parallel at the same time, for example, by using an array of nanopores containing an opaque layer. In some embodiments, nucleotides are labeled with fluorescent labels that are capable of at least three states while attached to a polynucleotide: (i) A substantially quenched state wherein fluorescence of an attached fluorescent label is quenched by a fluorescent label on an immediately adjacent monomer or by interaction with a quenching agent; for example, a fluorescent label attached to a polynucleotide in accordance with the invention is substantially quenched when the labeled polynucleotide is free in conventional aqueous solutions or buffers for studying and manipulating the polynucleotide. (ii) A sterically constrained state while a labeled polynucleotide is translocating through a nanopore such that the free-solution movements or alignments of attached fluorescent labels are disrupted or limited so that there is little or no detectable fluorescent signal generated from the fluorescent label. (iii) A transition state wherein fluorescent labels attached to a polynucleotide transition from the sterically constrained state to a quenched state as the nucleotide of the fluorescent label exits the nanopore (during a "transition interval" or "interval"). During the transition interval a fluorescent label (on an otherwise substantially fully labeled and self-quenched or quenched polynucleotide) is capable of generating a detectable fluorescent signal and that the number of exiting labels contributing to a measured signal may be (at least in part) controlled by controlling the translocation speed of the labeled polynucleotide. If translocation speed (e.g. nucleotides exiting a nanopore per msec) is higher than the transition rate (from signal-capable to quenched, i.e. the quenching rate), then measured fluorescent signals, or signal samples, may contain contributions from more than one label.

Without the intention of being limited by any theory underlying the above process, it is believed that the fluorescent signal generated during the transition interval is due to the presence of one or more freely rotatable dipoles of the fluorescent labels that emerged from a nanopore, which renders the fluorescent labels capable of generating a fluorescent signal, for example, after direct excitation or via excitation via FRET. In some embodiments, the polynucleotide is a single stranded polynucleotide, such as, DNA or RNA, but especially a single stranded DNA. In some embodiments, the invention includes a method for determining a nucleotide sequence of a polynucleotide by recording signals generated by fluorescent labels as they exit a nanopore one at a time as a polynucleotide translocates through the nanopore. A translocation speed may be selected to maximize the likelihood that measured fluorescent signals comprise fluorescence from substantially only a single label, wherein such selection may be made either by real-time adjustment of parameters controllable during operation (such as the voltage across the nanopores, temperature, or the like) or by predetermined instrument set-up (e.g. reaction buffer viscosity, ion concentration, or the like). Upon exit, each attached fluorescent label transitions during a transition interval from a constrained state in the nanopore to a quenched state on the polynucleotide in free solution. During the transition interval the label is capable of generating a fluorescent signal which can be measured. In other words, in some embodiments, a step of the method may comprise exciting each fluorescent label as it is transitioning from a constrained state in the nanopore to a quenched state on the polymer in free solution. As mentioned above, during this transition interval or period a fluorescent label is capable of emitting a detectable fluorescent signal indicative of the nucleotide to which it is attached.

In some embodiments, "substantially quenched" as used above means a fluorescent label generates a fluorescent signal at least thirty percent reduced from a signal generated under the same conditions, but without adjacent mutually quenching labels. In some embodiments, "substantially quenched" as used above means a fluorescent label generates a fluorescent signal at least fifty percent reduced from a signal generated under the same conditions, but without adjacent mutually quenching labels.

Figure 4A:
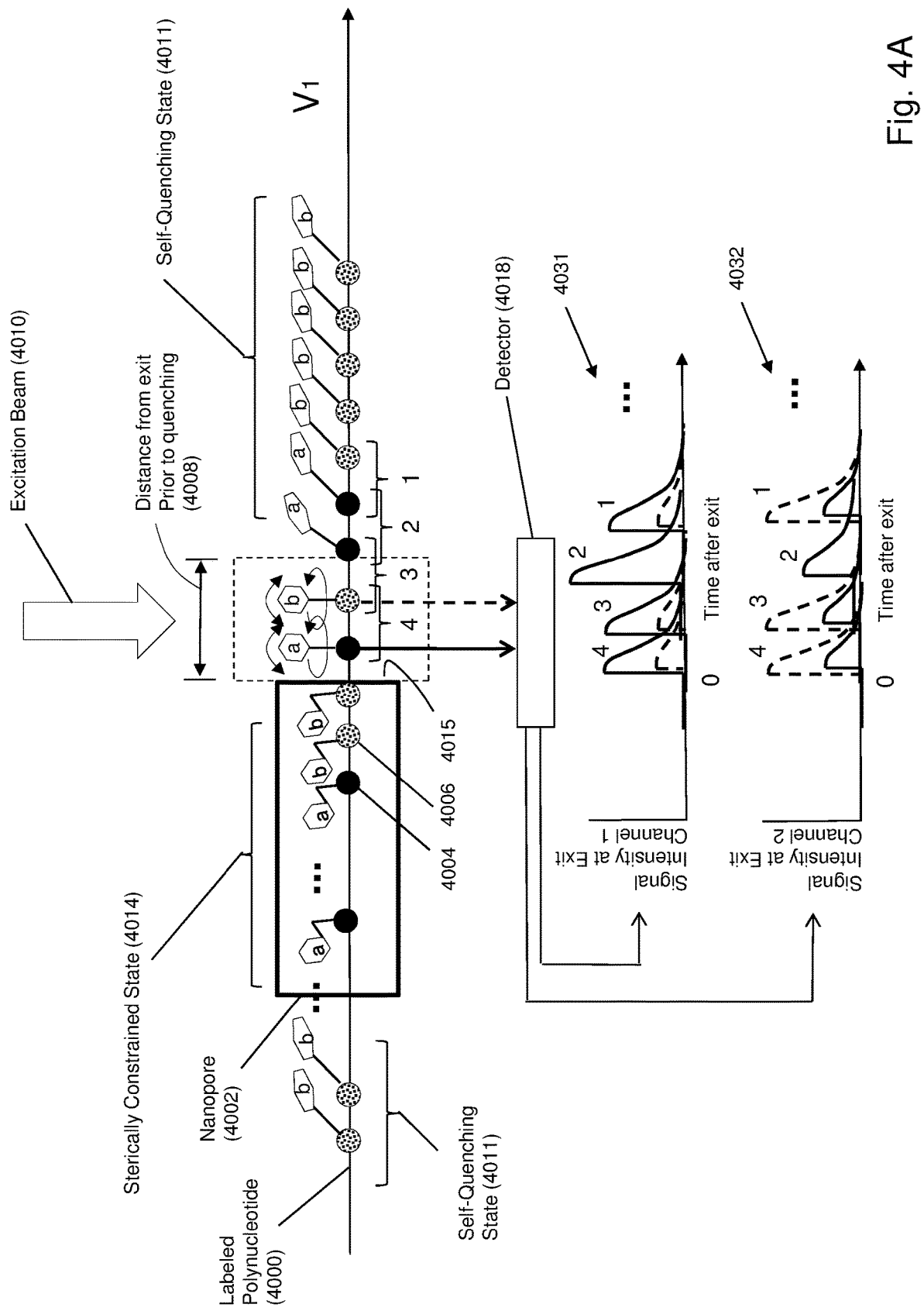
FIGS. 4A-4C illustrate a applications of nanopore arrays with opaque layers to methods of optically based nanopore sequencing using quenching.
Figure 4B:
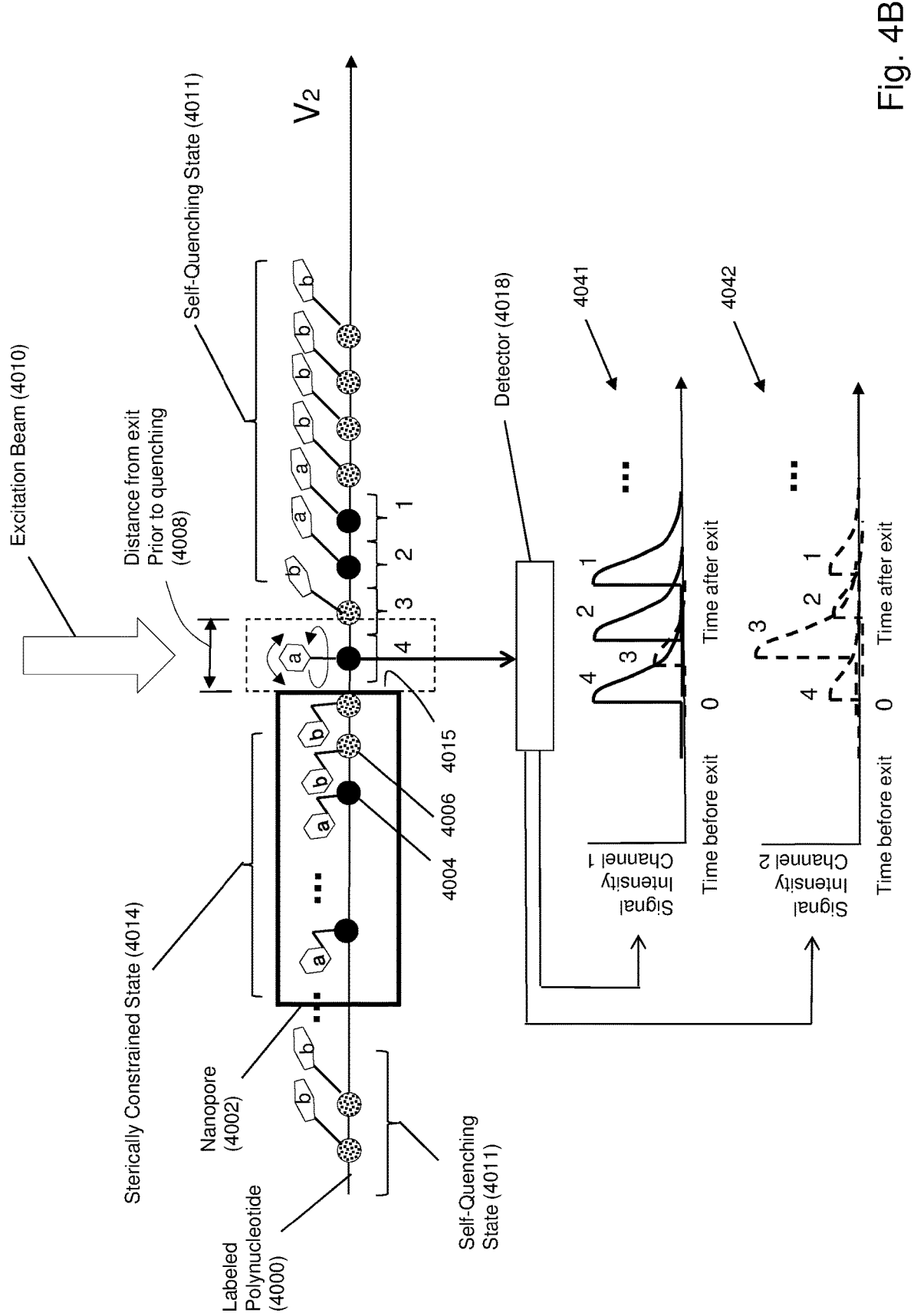

The above concepts are illustrated in FIGS. 4A-4B, which diagrammatically show labeled polynucleotide (4000) translocating through nanopore (4002). Labeled polynucleotide (4000) comprises two labels "a" and "b" (for example, which may correspond to dC being labeled with "a" and dA, dG and dT being labeled with "b", or the like). Labels of nucleotides free of nanopore (4002) are quenched, either by interaction with other labels (4011) or by action of quenching agents (not shown). Labels of nucleotides inside of nanopore (4002) are constrained and/or oriented (4014) so that they produce no detectable signal during all or part of their transit through the nanopore. As nucleotides of labeled polynucleotide (4000) emerge from exit (4015) of nanopore (4002) they become capable of being excited by excitation beam (4010) and generating a detectable signal for an interval prior to being quenched. If translocation speed $V_1$ is high then the distance (4008) traveled by a nucleotide prior to quenching may exceed the inter-nucleotide distance of polynucleotide (4000) so that more than one label (shown in FIG. 4A) contributes fluorescence to a fluorescent signal collected by detector (4018), i.e. a measured fluorescent signal. If translocation speed $V_2$ is low then the distance (4008) traveled by a nucleotide prior to quenching may approximately equal or be less than the inter-nucleotide distance of polynucleotide (4000) so that no more than one label (shown in FIG. 4B) contributes fluorescence to a fluorescent signal collected by detector (4018), i.e. a measured fluorescent signal. Since the distance between adjacent labels is below the diffraction limit of excitation light (4010) no information is obtained about the ordering of the labels, although there are approaches to deduce such information using specialized algorithms, e.g. Anderson et al, U.S. provisional patent application 62/322,343; Timp et al, Biophys. J., 102: L37-L39 (2012); Carson et al, Nanotechnology, 26: 074004 (2015). In the case of optical detection using fluorescent labels with distinct emission bands, measured fluorescent signals may be separated into two or more channels, e.g. using bandpass filters, in order to assess the relative contributions of fluorescence from multiple labels. However, as the number of fluorescent labels contributing fluorescence increases, e.g. 3, 4, or more, the difficulty in determining a correct ordering of nucleotides increases. The signal intensities for two channels, e.g. corresponding to emission maxima of two fluorescent labels, is illustrated in FIG. 4A (4031 and 4032) where two fluorescent labels contribute to a measured signal and in FIG. 4B (4041 and 4042) where a single fluorescent label contributes to a measured signal. Intensity values represented by solid lines, e.g. 4033, are from label "a," and intensity values represented by dashed lines, e.g. 4036, are from label "b". The presence of solid and dashed lines in both channels of FIG. 4A reflects overlapping emission bands of the fluorescent labels, which when collected together complicates analysis because amounts of a measured intensity are from both labels. In FIG. 4B, where only a single fluorescent label contributes to the measured signal, intensity values do not contain contributions due to overlapping emission bands of other labels, thereby making label (and therefore nucleotide) determination easier.

The role of translocation speed of polynucleotides through nanopores and the need for its control have been appreciated in the field of nanopore technology wherein changes in electric current are use to identify translocating analytes. A wide variety of methods have been used to control translocation speed, which include both methods that can be adjusted in real-time without significant difficulty (e.g. voltage potential across nanopores, temperature, and the like) and methods that can be adjusted during operation only with difficulty (reaction buffer viscosity, presence or absence of charged side chains in the bore of a protein nanopore, ionic composition and concentration of the reaction buffer, velocity-retarding groups attached or hybridized to polynucleotide analytes, molecular motors, and the like), e.g. Bates et al, Biophysical J., 84: 2366-2372 (2003); Carson et al, Nanotechnology, 26(7): 074004 (2015); Yeh et al, Electrophoresis, 33(23): 58-65 (2012); Meller, J. Phys. Cond. Matter, 15: R581-R607 (2003); Luan et al, Nanoscale, 4(4): 1068-1077 (2012); Keyser, J. R. Soc. Interface, 8: 1369-1378 (2011); and the like, which are incorporated herein by reference. In some embodiments, a step or steps may be included for active control of translocation speed while a method of the invention is being implemented, e.g. voltage potential, temperature, or the like; in other embodiments, a step or steps are included that determine a translocation speed that is not actively controlled or changed while a method of the invention is being implemented, e.g. reaction buffer viscosity, ionic concentration, and the like. In regard to the latter, in some embodiments, a translocation speed is selected by providing a reaction buffer having a concentration of glycerol, or equivalent reagent, in the range of from 1 to 60 percent.

In regard to the former embodiments (with real-time translocation speed adjustment), a measure of whether one or more than one label is contributing fluorescence to measured signals may be based on the distribution of fluorescence intensity among a plurality of channels over which fluorescence is collected. Typically the plurality of channels include 2, 3, or 4 channels corresponding to the emission bands of the fluorescent labels used. In a measured sample of fluorescence emanating from a region adjacent to a nanopore exit, if only a single label contributes to a measured signal, the relative distribution of signal intensity among the different channels (e.g. 4 channels) could be represented ideally as (1,0,0,0); (0,1,0,0); (0,0,1,0) or (0,0,0,1). On the other hand, if more than one label contributed to a measured fluorescent signal, the relative distributions would include non-zero values in more than one channel, with a worse case being four different labels contributing equally, which would appear as (0.25,0.25,0.25,0.25) in the above representation. A measure which would vary monotonically between a maximum value corresponding to relative intensity distributions (1,0,0,0); (0,1,0,0); (0,0,1,0) or (0,0,0,1) and a minimum value corresponding to a relative intensity distribution of (0.25,0.25,0.25,0.25) may be used for controlling in real-time a translocation speed. For example, an initial translocation speed could be lowered based on the value of such a measure that was near its minimum. Such lowering may be implemented, for example, by lowering a potential voltage across the nanopores by a predetermined amount, after which the measure could be re-calculated. Such steps could be repeated until the process was optimized.

As mentioned above, translocation speeds depend in part on the voltage difference (or electrical field strength) across a nanopore and conditions in the reaction mixture, or buffer, of a first chamber where polynucleotides are exposed to the nanopores (e.g. disposed in a solid phase membrane making up one wall of the first chamber). Polynucleotide capture rates by nanopores depend on concentration of such polynucleotides. In some embodiments, conventional reaction mixture conditions for nanopore sequencing may be employed with the invention (for controlling translocatin speed by varying voltage potential across nanopores), for example, 1M KCl (or equivalent salt, such as NaCl, LiCl, or the like) and a pH buffering system (which, for example, ensures that proteins being used, e.g. protein nanopores, nucleases, or the like, are not denatured). In some embodiments, a pH buffering system may be used to keep the pH substantially constant at a value in the range of 6.8 to 8.8. In some embodiments, a voltage difference across the nanopores may be in the range of from 70 to 200 mV. In other embodiments, a voltage difference across the nanopores may be in the range of from 80 to 150 mV. An appropriate voltage for operation may be selected using conventional measurement techniques. Current (or voltage) across a nanopore may readily be measured using commercially available instruments. A voltage difference may be selected so that translocation speed is within a desired range. In some embodiments, a range of translocation speeds comprises those speeds less than 1000 nucleotides per second. In other embodiments, a range of translocation speeds is from 10 to 800 nucleotides per second; in other embodiments, a range of translocation speeds is from 10 to 600 nucleotides per second; in other embodiments, a range of translocation speeds is from 200 to 800 nucleotides per second; in other embodiments, a range of translocation speeds is from 200 to 500 nucleotides per second. Likewise, other factors affecting translocation speed, e.g. temperature, viscosity, ion concentration, charged side chains in the bore of a protein nanopore, and the like, may be selected to obtain translocation speeds in the ranges cited above.

In some embodiments, a device for implementing the above methods for single stranded nucleic acids typically includes providing a set of electrodes for establishing an electric field across the nanopores (which may comprise an array). Single stranded nucleic acids are exposed to nanopores by placing them in an electrolyte (i.e. reaction buffer) in a first chamber, which is configured as the "cis" side of the layered membrane by placement of a negative electrode in the chamber. Upon application of an electric field, the negatively single stranded nucleic acids are captured by nanopores and translocated to a second chamber on the other side of the layered membrane, which is configured as the "trans" side of membrane by placement of a positive electrode in the chamber. As mentioned above, the speed of translocation depends in part on the ionic strength of the electrolytes in the first and second chambers and the applied voltage across the nanopores. In optically based detection, a translocation speed may be selected by preliminary calibration measurements, for example, using predetermined standards of labeled single stranded nucleic acids that generate signals at different expected rates per nanopore for different voltages. Thus, for DNA sequencing applications, an initial translocation speed may be selected based on the signal rates from such calibration measurements, as well as the measure based on relative signal intensity distribution discussed above. Consequently, from such measurements a voltage may be selected that permits, or maximizes, reliable nucleotide identifications, for example, over an array of nanopores. In some embodiments, such calibrations may be made using nucleic acids from the sample of templates being analyzed (instead of, or in addition to, predetermined standard sequences). In some embodiments, such calibrations may be carried out in real time during a sequencing run and the applied voltage may be modified in real time based on such measurements, for example, to maximize the acquisition of nucleotide-specific signals.

Embodiments Employing Mutually and Self-Quenching Labels

As mentioned above, in some embodiments, self- and mutually quenching fluorescent labels may be used in addition to quenching agents in order to reduce fluorescent emissions outside of those from labels on nucleotides exiting nanopores. Use of such fluorescent labels is disclosed in U.S. patent publication 2016/0122812, which is incorporated by reference. In some embodiments, monomers are labeled with fluorescent labels that are capable of at least three states while attached to a target polynucleotide: (i) A substantially quenched state wherein fluorescence of an attached fluorescent label is quenched by a fluorescent label on an immediately adjacent monomer; for example, a fluorescent label attached to a polynucleotide in accordance with the invention is substantially quenched when the labeled polynucleotide is free in conventional aqueous solution for studying and manipulating the polynucleotide. (ii) A sterically constrained state wherein a labeled polynucleotide is translocating through a nanopore such that the free-solution movements or alignments of an attached fluorescent label is disrupted or limited so that there is little or no detectable fluorescent signal generated from the fluorescent label. (iii) A transition state wherein a fluorescent label attached to a polynucleotide transitions from the sterically constrained state to the quenched state as the fluorescent label exits the nanopore (during a "transition interval") while the polynucleotide translocates through the nanopore.

In part, this example is an application of the discovery that during the transition interval a fluorescent label (on an otherwise substantially fully labeled and self-quenched polynucleotide) is capable of generating a detectable fluorescent signal. Without the intention of being limited by any theory underlying this discovery, it is believed that the fluorescent signal generated during the transition interval is due to the presence of a freely rotatable dipole in the fluorescent label emerging from the nanopore, which renders the fluorescent label temporarily capable of generating a fluorescent signal, for example, after direct excitation or via FRET. In both the sterically constrained state as well as the quenched state, the dipoles are limited in their rotational freedom thereby reducing or limiting the number of emitted photons. In some embodiments, the polynucleotide is a polynucleotide, usually a single stranded polynucleotide, such as, DNA or RNA, but especially single stranded DNA. In some embodiments, the invention includes a method for determining a nucleotide sequence of a polynucleotide by recording signals generated by attached fluorescent labels as they exit a nanopore one at a time as a polynucleotide translocates through the nanopore. Upon exit, each attached fluorescent label transitions during a transition interval from a constrained state in the nanopore to a quenched state on the polynucleotide in free solution. In other words, in some embodiments, a step of the method of the invention comprises exciting each fluorescent label as it is transitioning from a constrained state in the nanopore to a quenched state on the polynucleotide in free solution. As mentioned above, during this transition interval or period the fluorescent label is capable of emitting a detectable fluorescent signal indicative of the nucleotide it is attached to.

In some embodiments, the invention includes an application of the discovery that fluorescent labels and nanopores may be selected so that during translocation of a polynucleotide through a nanopore fluorescent labels attached to monomers are forced into a constrained state in which they are incapable (or substantially incapable) of producing a detectable fluorescent signal. In some embodiments, nanopores are selected that have a bore, or lumen, with a diameter in the range of from 1 to 4 nm; in other embodiments, nanopores are selected that have a bore or lumen with a diameter in the range of from 2 to 3 nm. In some embodiments, such bore diameters are provided by a protein nanopore. In some embodiments, such nanopores are used to force fluorescent labels into a constrained state in accordance with the invention, so that whenever a fluorescent label exits a nanopore, it transitions from being substantially incapable of generating a fluorescent signal to being detectable and identifiable by a fluorescent signal it can be induced to emit. Thus, fluorescent labels attached to each of a sequence of monomers of a polynucleotide may be detected in sequence as they suddenly generate a fluorescent signal in a region immediately adjacent to a nanopore exit (a "transition zone" or "transition volume" or "detection zone"). In some embodiments, organic fluorescent dyes are used as fluorescent labels with nanopores of the above diameters. In some embodiments, at least one such organic fluorescent dye is selected from the set consisting of xanthene dyes, rhodamine dyes and cyanine dyes. Some embodiments for determining a monomer sequence of a polynucleotide may be carried out with the following steps: (a) translocating a polynucleotide through a nanopore, wherein monomers of the polynucleotide are labeled with fluorescent labels wherein the nanopore constrains fluorescent labels within its bore into a constrained state such that substantially no detectable fluorescent signal is generated therein; (b) exciting the fluorescent label of each monomer upon exiting the nanopore; (c) measuring a fluorescent signal in a detection zone generated by the exiting fluorescent label to identify the monomer to which the fluorescent label is attached; (d) quenching fluorescent signals from excited fluorescent labels outside of the detection zone, and (d) determining a monomer sequence of the polynucleotide from a sequence of fluorescent signals. In further embodiments, fluorescent labels are acceptors of a FRET pair and one or more donors of the FRET pair are attached to the nanopore within a FRET distance of the exit.

In some embodiments, "substantially quenched" as used above means a fluorescent label generates a fluorescent signal at least thirty percent reduced from a signal generated under the same conditions, but without adjacent mutually quenching labels. In some embodiments, "substantially quenched" as used above means a fluorescent label generates a fluorescent signal at least fifty percent reduced from a signal generated under the same conditions, but without adjacent mutually quenching labels.

In some embodiments, a nucleotide sequence of a target polynucleotide is determined by carrying out four separate reactions in which copies of the target polynucleotide have each of its four different kinds of nucleotide (A, C, G and T) labeled with a single fluorescent label. In a variant of such embodiments, a nucleotide sequence of a target polynucleotide is determined by carrying out four separate reactions in which copies of the target polynucleotide have each of its four different kinds of nucleotide (A, C, G and T) labeled with one fluorescent label while at the same time the other nucleotides on the same target polynucleotide are labeled with a second fluorescent label. For example, if a first fluorescent label is attached to A's of the target polynucleotide in a first reaction, then a second fluorescent label is attached to C's, G's and T's (i.e. to the "not-A" nucleotides) of the target polynucleotides in the first reaction. Likewise, in continuance of the example, in a second reaction, the first label is attached to C's of the target polynucleotide and the second fluorescent label is attached to A's, G's and T's (i.e. to the "not-C" nucleotides) of the target polynucleotide. And so on, for nucleotides G and T.

The same labeling scheme may be expressed in terms of conventional terminology for subsets of nucleotide types; thus, in the above example, in a first reaction, a first fluorescent label is attached to A's and a second fluorescent label is attached to B's; in a second reaction, a first fluorescent label is attached to C's and a second fluorescent label is attached to D's; in a third reaction, a first fluorescent label is attached to G's and a second fluorescent label is attached to H's; and in a fourth reaction, a first fluorescent label is attached to T's and a second fluorescent label is attached to V's.

In some embodiments, a polymer, such as a polynucleotide or peptide, may be labeled with a single fluorescent label attached to a single kind of monomer, for example, every T (or substantially every T) of a polynucleotide is labeled with a fluorescent label, e.g. a cyanine dye. In such embodiments, a collection, or sequence, of fluorescent signals from the polynucleotide may form a signature or fingerprint for the particular polynucleotide. In some such embodiments, such fingerprints may or may not provide enough information for a sequence of monomers to be determined.

In some embodiments, a feature of the invention is the labeling of substantially all monomers of a polynucleotide analyte with fluorescent dyes or labels that are members of a mutually quenching set. The use of the term "substantially"

all" in reference to labeling polynucleotide analytes is to acknowledge that chemical and enzymatic labeling techniques are typically less than 100 percent efficient. In some embodiments, "substantially all" means at least 80 percent of all monomer have fluorescent labels attached. In other embodiments, "substantially all" means at least 90 percent of all monomer have fluorescent labels attached. In other embodiments, "substantially all" means at least 95 percent of all monomer have fluorescent labels attached. Mutually quenching sets of fluorescent dyes have the following properties: (i) each member quenches fluorescence of every member (for example, by FRET or by static or contact mechanisms), and (ii) each member generates a distinct fluorescent signal when excited and when in a non-quenched state. That is, if a mutually quenching set consists of two dyes, D1 and D2, then (i) D1 is self-quenched (e.g. by contact quenching with another D1 molecule) and it is quenched by D2 (e.g. by contact quenching) and (ii) D2 is self-quenched (e.g. by contact quenching with another D2 molecule) and it is quenched by D1 (e.g. by contact quenching). Guidance for selecting fluorescent dyes or labels for mutually quenching sets may be found in the following references, which are incorporated herein by reference: Johansson, Methods in Molecular Biology, 335: 17-29 (2006); Marras et al, Nucleic Acids Research, 30: e122 (2002); and the like. In some embodiments, members of a mutually quenching set comprise organic fluorescent dyes that components or moieties capable of stacking interactions, such as aromatic ring structures. Exemplary mutually quenching sets of fluorescent dyes, or labels, may be selected from rhodamine dyes, fluorescein dyes and cyanine dyes. In one embodiment, a mutually quenching set may comprise the rhodamine dye, TAMRA, and the fluorescein dye, FAM. In another embodiment, mutually quenching sets of fluorescent dyes may be formed by selecting two or more dyes from the group consisting of Oregon Green 488, Fluorescein-EX, fluorescein isothiocyanate, Rhodamine Red-X, Lissamine rhodamine B, Calcein, Fluorescein, Rhodamine, one or more BODIPY dyes, Texas Red, Oregon Green 514, and one or more Alexa Fluors. Respresentative BODIPY dyes include BODIPY FL, BODIPY R6G, BODIPY TMR, BODIPY 581/591, BODIPY TR, BODIPY 630/650 and BODIPY 650/665. Representative Alexa Fluors include Alexa Fluor 350, 405, 430, 488, 500, 514, 532, 546, 555, 568, 594, 610, 633, 635, 647, 660, 680, 700, 750 and 790.

As above, in some embodiments, a monomer sequence of a target polynucleotide is determined by carrying out separate reactions (one for each kind of monomer) in which copies of the target polynucleotide have each different kind of monomer labeled with a mutually- or self-quenching fluorescent label. In other embodiments, a monomer sequence of a target polynucleotide is determined by carrying out separate reactions (one for each kind of monomer) in which copies of the target polynucleotide have each different kind of monomer labeled with a different mutually quenching fluorescent label selected from the same mutually quenching set. In embodiments in which a mutually quenching set contains only two dyes, then a selected monomer (say, monomer X) is labeled with a first mutually quenching dye and every other kind of monomer (i.e., not-monomer X) is labeled with a second mutually quenching dye from the same set. Thus, steps of the embodiment generate a sequence of two different fluorescent signals, one indicating monomer X and another indicating not-monomer X.

In some embodiments, a single fluorescent label (for example, attached to a single kind of monomer in a polynucleotide comprising multiple kinds of monomers) may be used that is self-quenching when attached to adjacent monomers (of the same kind) on a polynucleotide, such as adjacent nucleotides of a polynucleotide. Exemplary self-quenching fluorescent labels include, but are not limited to, Oregon Green 488, fluorescein-EX, FITC, Rhodamine Red-X, Lissamine rhodamine B, calcein, fluorescein, rhodamine, BODIPYS, and Texas Red, e.g. which are disclosed in Molecular Probes Handbook, 11th Edition (2010).

Embodiments Employing Quenching Agents

Figure 4C:
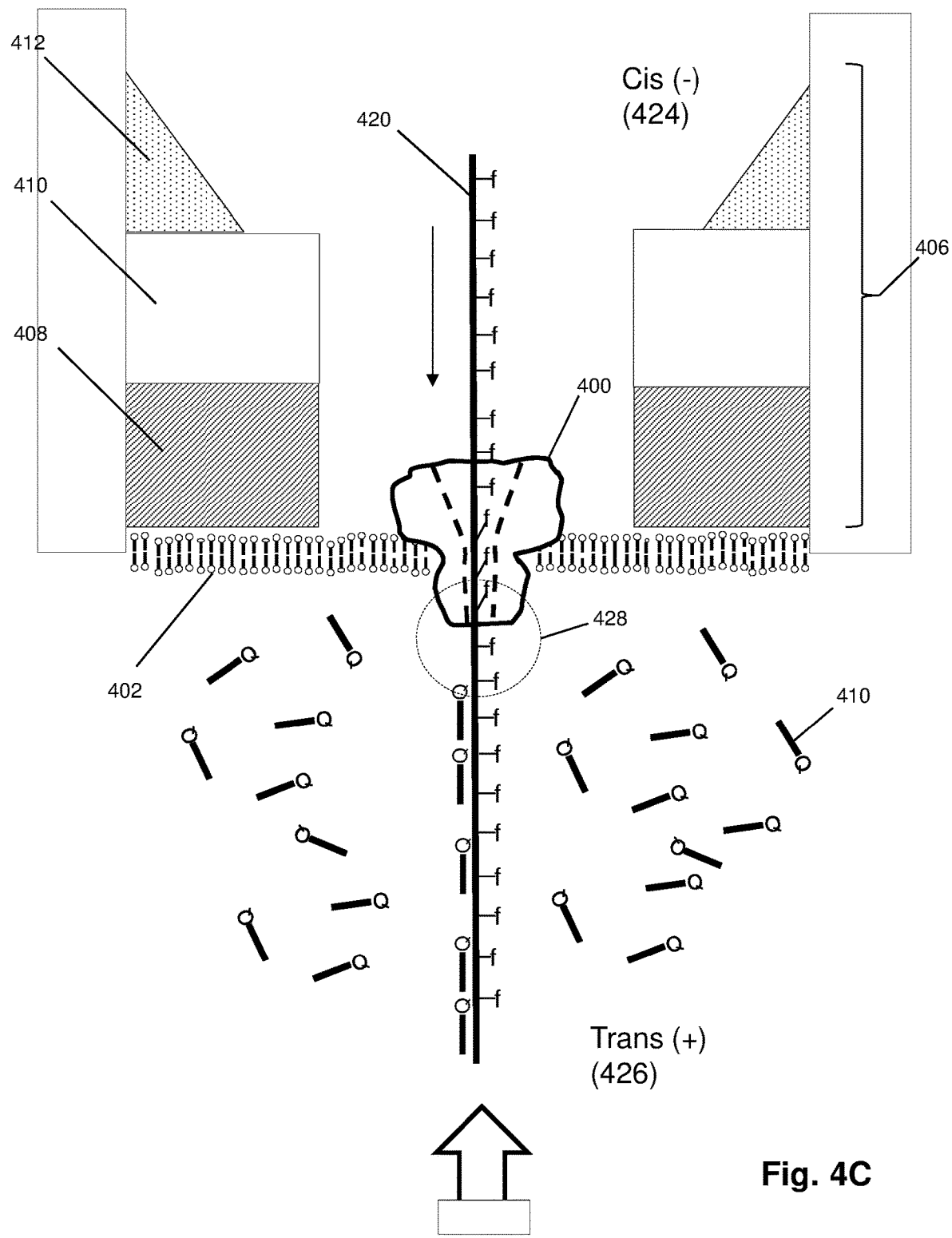

As explained more fully below, a large variety of non-fluorescent quenching agents are available for use with the invention, which include derivatives of many well-known organic dyes, such as asymmetric cyanine dyes, as well as conjugates of such compounds and oligonucleotides and/or analogs thereof. Quenching agents may be disposed in either the cis chamber, the trans chamber, or both. FIG. 4C illustrates an embodiment which includes the following elements: protein nanopore (400) disposed in lipid bilayer (402); epi-illumination of fluorescent labels with opaque layer (408) in solid phase membrane (406) to prevent or reduce background fluorescence; and quenching agents (410) disposed in trans chamber (426). As above, polynucleotide (420) with fluorescently labeled nucleotides (labels being indicated by "f", as with (422)) is translocated through nanopore (400) from cis chamber (424) to trans chamber (426). Oligonucleotide quenchers (410) are disposed in trans chamber (426) under conditions (e.g. concentration, temperature, salt concentration, and the like) that permits hybridization of oligonucleotide quenchers (428) to portions of polynucleotide (420) emerging from nanopore (400). Nanopore (400) may be selected so that signals from fluorescent labels are suppressed during transit of the nanopore as described in Huber et al, U.S. patent publication US 2016/0076091, which is incorporated herein by reference. Thus, when labeled nucleotides emerge from nanopore (400) in region (428) they become unsuppressed and capable of generating a signal. With most if not all forms of direct illumination (e.g. non-FRET) such emerged labels would continue to emit fluorescence as they travel further into trans chamber (426), thereby contributing greatly to a collected signal. With quenching agents in trans chamber (426) that bind to the emerging polynucleotide, such emissions can be significantly reduced and can define detection zone (428) from which collected signals can be analyzed to give nucleotide sequence information about polynucleotide (420). In some embodiments, a fluorescent signal from a single fluorescent label is detected from detection zone (428) during a detection period as the labeled polynucleotide moves through the detection zone. In other embodiments, a plurality of fluorescent signals is collected from a plurality of fluorescent labels in detection zone (428) during a predetermined time period. In some embodiments, such detection period is less than 1 msec, or less than 0.1 msec, or less than 0.01 msec. In some embodiments, such detection perior is at least 0.01 msec, or at least 0.1 msec, or at least 0.5 msec.

Quenching agents of the invention comprise any compound (or set of compounds) that under nanopore sequencing conditions is (i) substantially non-fluorescent, (ii) binds to single stranded nucleic acids, particularly single stranded DNA, and (iii) absorbs excitation energy from other molecules non-radiatively and releases it non-radiatively. In some embodiments, quenching agents further bind non-covalently to single stranded DNA. A large variety of quenching compounds are available for use with the invention including, but not limited to, non-fluorescent derivatives of common synthetic dyes such as cyanine and xanthene dyes, as described more fully below. Guidance in selecting quenching compounds may be found in U.S. Pat. Nos. 6,323,337; 6,750,024 and like references, which are incorporated herein by reference.

In some embodiments, a quenching agent may be a single stranded DNA binding dye that has been covalently modified with a heavy atom that is known to quench fluorescence (such as bromine or iodine), or covalently modified with other groups known to quench fluorescence, such as a nitro group or a azo group. An example of dye that is known to bind single stranded DNA is Sybr Green (Zipper et al, (2004), Nucleic Acids Research. 32 (12)). Incorporation of a nitro, bromine, iodine, and/or azo groups into the cynanine Sybr Green structure provides a single stranded DNA binding group moiety that will quench fluorescent labels that might be present on a DNA.

In some embodiments, quenching agents comprise a binding moiety and one or more quenching moieties. Binding moieties may include any compound that binds to single stranded nucleic acids without substantial sequence specificity. Binding moieties may comprise peptides or oligonucleotides or analogs of either having modified linkages and/or monomers. Oligonucleotides and their analogs may provide binding to polynucleotides via duplex formation or via non-base paired aptameric binding. In some embodiments, binding moieties comprise an oligonucleotide or analog thereof having a length in the range of from 6 to 60 nucleotides. Such oligonucleotides or analogs may be conjugated to one quenching moiety or to a plurality of quenching moieties. In some embodiments, the plurality of quenching moieties conjugated to each oligonucleotide or analog is 2 or 3. Quenching moieties conjugated to a binding moiety may be the same or different. In some embodiments, whenever a binding moiety is an oligonucleotide or analog, two quenching moieties are conjugated thereto, one at a 5' end and one at a 3' end of the oligonucleotide. Oligonucleotides or analogs having from 2 to 3 quenching moieties may be synthesized using conventional linkage and synthetic chemistries, for example, as disclosed in the references cited herein.

Oligonucleotides or analogs may be provided as a single species or they may be provided as mixtures of a plurality of oligonucleotides or analogs with different sequences, and therefore, different binding specificities. In some embodiments, oligonucleotides or analogs are random sequence polymers; that is, they are provided as mixtures of every possible sequence of a given length. For example, such oligonucleotides or analogs may be represented by the formulas, "NNNNNN" for 6-mers, or "NNNNNNNN" for 8-mers, wherein N may be A, C, G or T, or an analog thereof.

"Analogs" in reference to oligonucleotides means an oligonucleotide that contains one or more nucleotide analogs. As described in the definition section, a "nucleotide analog" is a nucleotide that may have a modified linkage moiety, sugar moiety or base moiety. Exemplary oligonucleotide analogs that may be used with the invention include, but are not limited to, peptide nucleic acids (PNAs), locked nucleic acids (LNAs)(2'-O-methyl RNA), phosphorothioate oligonucleotides, bridged nucleic acids (BNAs), or the like.

In some embodiments, oligonucleotide binding moieties comprise universal bases; that is, they contain one or more nucleotide analogs that can replace any of the four natural nucleotides without destabilizing base-pair interactions. Nucleotide analogs having universal base properties are described in Loakes, Nucleic Acids Research, 29(12): 2437-2447 (2001), which is incorporated herein by reference. In some embodiments, oligonucleotide binding moieties comprise 2'-deoxyinosine, 7-deaza-2'-deoxyinosine, 2-aza-2'-deoxyinosine, 3-nitropyrrole nucleotides, 5-nitroindole nucleotides, or the like.

In some embodiments, quenching agents may comprise a combination of two or more compounds that act together to quench undesired fluorescent signals of a single stranded labeled polynucleotide. For example, a quenching agent may comprise an oligonucleotide (e.g., polydeoxyinosine) that may form a duplex with the labeled polynucleotide and separately a double stranded intercalator that is a quencher. Thus, whenever the polydeoxyinosine binds to a labeled polynucleotide, the quenching intercalator binds to the resulting duplex and quenches fluorescent signals from the polynucleotide.

Any synthetic dye that can detectably quench fluorescent signals of the fluorescent labels of a labeled polynucleotide is an acceptable quenching moiety for the purposes of the invention. Specifically, as used in the invention, the quenching moieties possess an absorption band that exhibits at least some spectral overlap with an emission band of the fluorescent labels on a labeled polynucleotide. This overlap may occur with emission of the fluorescent label (donor) occurring at a lower or even higher wavelength emission maximum than the maximal absorbance wavelength of the quenching moiety (acceptor), provided that sufficient spectral overlap exists. Energy transfer may also occur through transfer of emission of the donor to higher electronic states of the acceptor. One of ordinary skill in the art determines the utility of a given quenching moiety by examination of that dye's excitation bands with respect to the emission spectrum of the fluorescent labels being used.

Typically, fluorescence quenching in the invention occurs through Fluorescence Resonance Energy Transfer (FRET or through the formation of charge transfer complexes) between a fluorescent label and a quenching moiety of the invention. The spectral and electronic properties of the donor and acceptor compounds have a strong effect on the degree of energy transfer observed, as does the separation distance between the fluorescent labels on the labeled polynucleotide and the quenching moiety. As the separation distance increases, the degree of fluorescence quenching decreases.

A quenching moiety may be optionally fluorescent, provided that the maximal emission wavelength of the dye is well separated from the maximal emission wavelength of the fluorescent labels when bound to labeled polynucleotides. Preferably, however, the quenching moiety is only dimly fluorescent, or is substantially non-fluorescent, when covalently conjugated to a oligonucleotide or analog. Substantially non-fluorescent, as used herein, indicates that the fluorescence efficiency of the quenching moiety in an assay solution as described for any of the methods herein is less than or equal to 5 percent, preferably less than or equal to 1 percent. In other embodiments, the covalently bound quenching moiety exhibits a quantum yield of less than about 0.1, more preferably less than about 0.01. In some embodiments, the fluorescence of fluorescent labels associated with a quenching oligonucleotide of the invention is quenched more than 50% relative to the same oligonucleotide associated with the same fluorescent labels in the absence of the covalently bound quenching moiety. In another embodiment, the fluorescent labels are quenched more than 90% relative to the unlabeled oligonucleotide. In yet another embodiment, the nucleic acid stains are quenched more than 95% relative to the unlabeled oligonucleotide.

In some embodiments, a quenching moiety may be a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated and sulfonated derivatives thereof (as described in U.S. Pat. No. 5,830,912 to Gee et al. (1998) and U.S. Pat. No. 5,696,157 to Wang et al. (1997), incorporated by reference), a polyazaindacene (e.g. U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); U.S. Pat. No. 5,433,896 to Kang, et al. (1995); U.S. Pat. No. 6,005,113 to Wu et al. (1999), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference).

In other embodiments, quenching moieties that are substantially non-fluorescent dyes include in particular azo dyes (such as DABCYL or DABSYL dyes and their structural analogs), triarylmethane dyes such as malachite green or phenol red, 4',5z-diether substituted fluoresceins (U.S. Pat. No. 4,318,846 (1982)), or asymmetric cyanine dye quenchers (PCT Int. App. WO 99 37,717 (1999)).

In embodiments where the quenching moiety is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171 to Haugland, et al. (1990), incorporated by reference). Xanthenes include fluorinated derivatives of xanthene dyes (Int. Publ. No. WO 97/39064, Molecular Probes, Inc. (1997), incorporated by reference), and sulfonated derivatives of xanthene dyes (Int. Publ. No. WO 99/15517, Molecular Probes, Inc. (1999), incorporated by reference). As used herein, oxazines include resorufms, aminooxazinones, diaminooxazines, and their benzo-substituted analogs.

In further embodiments, the quenching moiety is an substantially nonfluorescent derivative of 3- and/or 6-amino xanthene that is substituted at one or more amino nitrogen atoms by an aromatic or heteroaromatic ring system, e.g. as described in U.S. Pat. No. 6,399,392, which is incorporated herein by reference. These quenching dyes typically have absorption maxima above 530 nm, have little or no observable fluorescence and efficiently quench a broad spectrum of luminescent emission, such as is emitted by chemiluminphores, phosphors, or fluorophores. In one embodiment, the quenching dye is a substituted rhodamine. In another embodiment, the quenching compound is a substituted rhodol.

In still other embodiments, a quenching moiety may comprise one or more non-fluorescent quenchers known as Black Hole Quenchers™ compounds (BHQs) described in the following patents, which are incorporated herein by reference: U.S. Pat. Nos. 7,019,129; 7,109,312; 7,582,432; 8,410,025; 8,440,399; 8,633,307; 8,946,404; 9,018,369; or 9,139,610.

Additional quenching moieties are disclosed in the following, which are incorporated herein by reference: U.S. Pat. Nos. 6,699,975; 6,790,945; and 8,114,979.

EXAMPLE

Translocation of Target Polynucleotide in an Optically-Based Nanopore Sequencing Method In this example, the invention is used in conjunction with an exemplary optically-based nanopore sequencing method. In the exemplary optically-based nanopore sequencing method, nucleotides of target polynucleotides are labeled with fluorescent labels that are capable of at least three states: (i) A quenched state wherein fluorescence of an attached fluorescent label is quenched by a fluorescent label on an immediately adjacent nucleotide; for example, a fluorescent label attached to a polynucleotide is quenched when the labeled polynucleotide is free in an aqueous solution. (ii) A sterically constrained state wherein a labeled polynucleotide is translocating through a nanopore such that the free-solution movements or alignments of an attached fluorescent label is disrupted or limited so that there is little or no detectable signal generated from the fluorescent label. (iii) A transition state wherein a fluorescent label attached to a polynucleotide transitions from the sterically constrained state to the quenched state as the fluorescent label exits the nanopore (during a "transition interval") while the polynucleotide translocates through the nanopore. A nucleotide sequence of a polynucleotide is determined by recording signals generated by attached fluorescent labels as they exit a nanopore one at a time as a polynucleotide translocates the nanopore. Upon exit, each attached fluorescent label transitions during a transition interval from a constrained state in the nanopore to a quenched state on the polynucleotide in free solution. During this transition interval the fluorescent label is capable of emitting a detectable fluorescent signal indicative of the nucleotide it is attached to.

In some embodiments, the invention may be used with such a nanopore sequencing method using the following steps: (a) extending a primer having a 5' non-complementary tail on a template in a reaction mixture to produce a double stranded product comprising an extended strand and the 5' non-complementary tail as a single stranded overhang; (b) providing a nanopore (or an array of nanopores) that separates and provides fluid communication between a first chamber and a second chamber, wherein the nanopore is capable of passing a single stranded nucleic acid but not a double stranded nucleic acid; (c) disposing the double stranded product in the first chamber; (d) capturing the 5' non-complementary tail of the isolated double stranded product by the nanopore by applying an electrical field across the nanopore; (e) translocating a polymer analyte through a nanopore having a bore and an exit, the polymer analyte comprising a sequence of monomers, wherein substantially each monomer is labeled with a fluorescent label such that fluorescent labels of adjacent monomers are in a quenched state by self-quenching one another outside of the nanopore and fluorescent labels are in a sterically constrained state and incapable of generating a detectable fluorescent signal inside of the nanopore; (f) exciting each fluorescent label at the exit of the nanopore as it transitions from a sterically constrained state to a quenched state so that a fluorescent signal is generated which is indicative of the monomer to which it is attached; (g) detecting the fluorescent signal to identify the monomer. As used herein, "substantially every", "substantially all", or like terms, in reference to labeling monomers, particularly nucleotides, acknowledges that chemical labeling procedures may not result in complete labeling of every monomer; to the extent practicable, the terms comprehend that labeling reactions in connection with the invention are continued to completion; in some embodiments, such completed labeling reactions include labeling at least fifty percent of the monomers; in other embodiments, such labeling reactions include labeling at least eighty percent of the monomers; in other embodiments, such labeling reactions include labeling at least ninety-five percent of the monomers; in other embodiments, such labeling reactions include labeling at least ninety-nine percent of the monomers.

In some embodiments of the above method, fluorescent labels are members of a FRET pair. A FRET pair generally is one or more FRET donors and one or more FRET acceptors where each donor is capable of a FRET reaction with each acceptor. In one aspect, this means that the donors of the FRET pair have an emission spectrum that substantially overlaps the absorption spectrum of the acceptors. In another aspect, the transition dipole of the donor and the acceptor have to be aligned in a way that allows efficient energy transfer. In some aspects, the invention in part is based on the discovery and appreciation of a fluorescence, particularly, FRET suppressing property of nanopores and the application of this property to enable detection of labeled polymers translocating through a nanopore. It is believed, although the invention is not intended to be limited thereby, that a nanopore may be selected with a bore dimensioned so that a FRET pair label cannot orient to engage in a FRET interaction while translocating through the nanopore. The dipoles of the labels of the polynucleoide in the bore of the nanopore are constrained in their rotational freedom based on the limited diameter of the nanopore. This reduction in dipole alignment with the alignment of the corresponding FRET pair attached to the nanopore limits the FRET efficiency dramatically. Labeled polynucleotides can engage in a FRET interaction after exiting the nanopore at which point the FRET acceptor or donor on the polymer (e.g. polynucleotide) regains rotational freedom which allows for a FRET event.

Definitions

"FRET" or "Förster, or fluorescence, resonant energy transfer" means a non-radiative dipole-dipole energy transfer mechanism from an excited donor fluorophore to an acceptor fluorophore in a ground state. The rate of energy transfer in a FRET interaction depends on the extent of spectral overlap of the emission spectrum of the donor with the absorption spectrum of the acceptor, the quantum yield of the donor, the relative orientation of the donor and acceptor transition dipoles, and the distance between the donor and acceptor molecules, Lakowitz, Principles of Fluorescence Spectroscopy, Third Edition (Springer, 2006). FRET interactions of particular interest are those which result a portion of the energy being transferred to an acceptor, in turn, being emitted by the acceptor as a photon, with a frequency lower than that of the light exciting its donor (i.e. a "FRET signal"). "FRET distance" means a distance between a FRET donor and a FRET acceptor over which a FRET interaction can take place and a detectable FRET signal produced by the FRET acceptor.

"Kit" refers to any delivery system for delivering materials or reagents for carrying out a method of the invention. In the context of reaction assays, such delivery systems include systems that allow for the storage, transport, or delivery of reaction reagents (e.g., fluorescent labels, such as mutually quenching fluorescent labels, fluorescent label linking agents, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels.

"Nanopore" means any opening positioned in a substrate that allows the passage of analytes through the substrate in a predetermined or discernable order, or in the case of polymer analytes, passage of their monomeric units through the substrate in a pretermined or discernible order. In the latter case, a predetermined or discernible order may be the primary sequence of monomeric units in the polymer. Examples of nanopores include proteinaceous or protein based nanopores, synthetic or solid state nanopores, and hybrid nanopores comprising a solid state nanopore having a protein nanopore embedded therein. A nanopore may have an inner diameter of 1-10 nm or 1-5 nm or 1-3 nm. Examples of protein nanopores include but are not limited to, alpha-hemolysin, voltage-dependent mitochondrial porin (VDAC), OmpF, OmpC, MspA and LamB (maltoporin), e.g. disclosed in Rhee, M. et al., Trends in Biotechnology, 25(4) (2007): 174-181; Bayley et al (cited above); Gundlach et al, U.S. patent publication 2012/0055792; and the like, which are incorporated herein by reference. Any protein pore that allows the translocation of single nucleic acid molecules may be employed. A nanopore protein may be labeled at a specific site on the exterior of the pore, or at a specific site on the exterior of one or more monomer units making up the pore forming protein. Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into the solid state hole is accomplished by attaching a charged polymer to the pore protein. After applying an electric field the charged complex is electrophoretically pulled into the solid state hole. A synthetic nanopore, or solid-state nanopore, may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane. A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83). The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition. In some embodiments, single nanopores are employed with methods of the invention. In other embodiments, a plurality of nanopores are employed. In some of the latter embodiments, a plurality of nanopores is employed as an array of nanopores, usually disposed in a planar substrate, such as a solid phase membrane. Nanopores of a nanopore array may be spaced regularly, for example, in a rectilinear pattern, or may be spaced randomly. In a preferred embodiment, nanopores are spaced regularly in a rectilinear pattern in a planar solid phase substrate.

"Nanostructure" (used interchangeably with "nanoscale structure" and "nanoscale feature") means a structure that has at least one dimension within a range of a few nanometers to several hundred nanometers, for example, from 1 to 1000 nanometers. In some applications, such range is from 2 to 500 nanometers; in other applications, such range is from 3 to 500 nanometers. The shape and geometry of nanostructures may vary widely and include, but are not limited to, nanopores, nanowells, nanoparticles, and any other convenient shapes particularly suitable for carrying out sequences of reactions. In some embodiments, nanostructures may be protein nanopores operationally associated with a solid phase membrane. Some nanostructures, such as, nanopores and nanowells, may be formed in a larger common substrate, such as a solid phase membrane, or other solid, to form arrays of nanopores or nanowells. Nanostructures of particular interest are those capable of supporting or containing a chemical, physical (e.g. FRET), enzymatic and/or binding reaction or a sequence of such reactions. In some embodiments, a nanostructure, such as a nanowell, encloses a volume that is less than one nanoliter (10×−9 liter), less than one picoliter, or less than one femtoliter. In other embodiments, each of the individual nanowells provides a volume that is less than 1000 zeptoliters, 100 zeptoliters, 80 zeptoliters, or less than 50 zeptoliters, or less than 1 zeptoliter, or even less than 100 yactoliters. In some embodiments, nanowells comprise zero mode waveguides.

"Peptide," "peptide fragment," "polypeptide," "oligopeptide," or "fragment" in reference to a peptide are used synonymously herein and refer to a compound made up of a single unbranched chain of amino acid residues linked by peptide bonds. Amino acids in a peptide or polypeptide may be derivatized with various moieties, including but not limited to, polyethylene glycol, dyes, biotin, haptens, or like moieties. The number of amino acid residues in a protein or polypeptide or peptide may vary widely; however, in some embodiments, protein or polypeptides or peptides referred to herein may have 2 from to 70 amino acid residues; and in other embodiments, they may have from 2 to 50 amino acid residues. In other embodiments, proteins or polypeptides or peptides referred to herein may have from a few tens of amino acid residues, e.g. 20, to up to a thousand or more amino acid residues, e.g. 1200. In still other embodiments, proteins, polypeptides, peptides, or fragments thereof, may have from 10 to 1000 amino acid residues; or they may have from 20 to 500 amino acid residues; or they may have from 20 to 200 amino acid residues.

"Polymer" means a plurality of monomers connected into a linear chain. Usually, polymers comprise more than one type of monomer, for example, as a polynucleotide comprising A's, C's, G's and T's, or a polypeptide comprising more than one kind of amino acid. Monomers may include without limitation nucleosides and derivatives or analogs thereof and amino acids and derivatives and analogs thereof. In some embodiments, polymers are polynucleotides, whereby nucleoside monomers are connected by phosphodiester linkages, or analogs thereof.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence determination", "sequencing" or "determining a nucleotide sequence" or like terms in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)(not c)c-(not c)-c . . . " and the like. In some embodiments, the terms may also include subsequences of a target polynucleotide that serve as a fingerprint for the target polynucleotide; that is, subsequences that uniquely identify a target polynucleotide, or a class of target polynucleotides, within a set of polynucleotides, e.g. all different RNA sequences expressed by a cell.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method of determining sequences of polynucleotides, the method comprising:

providing a nanopore array comprising (a) a first side and a second side, (b) a solid phase membrane and an opaque layer co-extensive therewith, and (c) a plurality of apertures, the solid phase membrane separating a first chamber on the first side of the nanopore array and a second chamber on the second side of the nanopore array, wherein each aperture provides fluid communication between the first chamber and the second chamber and has a signal generation region and wherein the opaque layer substantially prevents light from passing through the nanopore array;

translocating polynucleotides from the first chamber to the second chamber through the apertures, wherein (i) each polynucleotide comprises a polynucleotide strand in which different kinds of nucleotides of the polynucleotide strand are labeled with different fluorescent labels that generate distinguishable fluorescent signals, (ii) each of said apertures constrains nucleotides of each said polynucleotide strand to move single file through the signal generation region of each aperture; and (iii) the fluorescent labels of each polynucleotide strand are mutually self-quenching, such that fluorescent signals from excited mutually self-quenching labels are quenched when the labels are outside of the signal generation region;

exciting with an excitation beam the fluorescent labels of the polynucleotide strands as they translocate through the signal generation regions of the apertures, wherein the excitation beam is directed to said nanopore array through said second chamber so that said metal layer substantially prevents excitation of optical labels in said first chamber;

detecting fluorescent signals from the fluorescent labels in the signal generation regions to determine the characteristics of the polynucleotide strands; and determining a sequence of nucleotides of the polynucleotide strands from the fluorescent signals detected at the signal generation region of each aperture.

2. The method of claim 1 wherein said opaque layer is a metal layer.

3. The method of claim 2 wherein said metal layer comprises an aluminum layer or a gold layer.

4. The method of claim 2 wherein said signal generation region of each of said apertures extends from a surface of said metal layer closest to said second chamber into said second chamber.

5. The method of claim 2 wherein said steps of exciting and detecting are implemented with an epi-illumination system.

6. The method of claim 2 wherein each of said apertures of said nanopore array comprises a protein nanopore immobilized therein.

7. The method of claim 6 wherein each of said protein nanopores are immobilized in a lipid bilayer disposed across said apertures.

8. The method of claim 2 wherein said fluorescent labels are acceptor labels and wherein said excitation beam excites a donor label at each of said apertures which donor labels excite the acceptor labels as they translocate through said signal generation region.

* * * * *